United States Patent
Kaufmann et al.

(10) Patent No.: US 11,426,487 B2
(45) Date of Patent: Aug. 30, 2022

(54) PROPERTY CHANGING IMPLANT

(71) Applicant: SetBone Medical Ltd., Doar-Na Misgav (IL)

(72) Inventors: Nimrod Kaufmann, Modi'in-Maccabim-Re'ut (IL); Royi Kaufmann, Hod-HaSharon (IL)

(73) Assignee: SetBone Medical Ltd., Ness Ziona (IL)

( * ) Notice: Subject to any disclaimer, the term of this patent is extended or adjusted under 35 U.S.C. 154(b) by 0 days.

(21) Appl. No.: 16/500,417

(22) PCT Filed: Apr. 4, 2018

(86) PCT No.: PCT/IL2018/050402
§ 371 (c)(1),
(2) Date: Oct. 3, 2019

(87) PCT Pub. No.: WO2018/185770
PCT Pub. Date: Oct. 11, 2018

(65) Prior Publication Data
US 2020/0139005 A1    May 7, 2020

Related U.S. Application Data

(60) Provisional application No. 62/530,400, filed on Jul. 10, 2017, provisional application No. 62/481,688, filed on Apr. 5, 2017.

(51) Int. Cl.
*A61L 27/16* (2006.01)
*A61L 27/18* (2006.01)
*A61L 27/56* (2006.01)

(52) U.S. Cl.
CPC ............... *A61L 27/16* (2013.01); *A61L 27/18* (2013.01); *A61L 27/56* (2013.01); *A61L 2430/02* (2013.01); *A61L 2430/24* (2013.01)

(58) Field of Classification Search
CPC ...................................... A61L 27/38
See application file for complete search history.

(56) References Cited

U.S. PATENT DOCUMENTS

| 2,609,347 | A | 9/1952 | Wilson |
| 4,670,506 | A | 6/1987 | Goldenberg et al. |
| 6,332,894 | B1 | 12/2001 | Stalcup et al. |

(Continued)

FOREIGN PATENT DOCUMENTS

| CN | 101966409 | 2/2011 |
| WO | WO 99/42528 | 8/1999 |

(Continued)

OTHER PUBLICATIONS

Communication Pursuant to Article 94(3) EPC dated Jan. 26, 2021 From the European Patent Office Re. Application No. 18722740.0. (7 Pages).

(Continued)

*Primary Examiner* — Yashita Sharma

(57) ABSTRACT

The present invention relates to implants comprising a deformable body formed of a polymer comprising functional groups capable of cross-linking to form a cross-link; said body provided in a first configuration which is cross-linked to a second configuration upon application of a selected stimuli; wherein said selected stimuli causes said cross-linking of said functional groups.

26 Claims, 16 Drawing Sheets

(56) References Cited

U.S. PATENT DOCUMENTS

| | | | |
|---|---|---|---|
| 6,340,648 B1 | 1/2002 | Imura et al. | |
| 6,476,087 B1 | 11/2002 | De Toffol | |
| 7,329,414 B2 * | 2/2008 | Fisher | A61L 24/0015 424/1.11 |
| 7,771,476 B2 | 8/2010 | Justis et al. | |
| 2004/0220672 A1 | 11/2004 | Shadduck | |
| 2006/0058891 A1 | 3/2006 | Lesh | |
| 2007/0129456 A1 | 6/2007 | Cha et al. | |
| 2009/0149954 A1 | 6/2009 | Hu et al. | |
| 2010/0010114 A1 * | 1/2010 | Myung | C08F 283/02 523/114 |
| 2010/0075056 A1 | 3/2010 | Axisa et al. | |
| 2010/0112032 A1 | 5/2010 | Guelcher et al. | |
| 2010/0178488 A1 | 7/2010 | Yasuda et al. | |
| 2011/0275727 A1 | 11/2011 | Yamamoto et al. | |
| 2011/0319510 A1 | 12/2011 | Tsuchiyama et al. | |
| 2012/0179193 A1 * | 7/2012 | Cohn | A61L 31/06 606/198 |
| 2013/0165575 A1 | 6/2013 | Jeong et al. | |
| 2016/0287516 A1 | 10/2016 | Cosgriff-Hernandez et al. | |

FOREIGN PATENT DOCUMENTS

| | | |
|---|---|---|
| WO | WO 2009/087610 | 7/2009 |
| WO | WO 2011/007352 | 1/2011 |
| WO | WO 2018/185770 | 10/2018 |

OTHER PUBLICATIONS

International Preliminary Report on Patentability dated Oct. 17, 2019 From the International Bureau of WIPO Re. Application No. PCT/IL2018/050402. (10 Pages).

International Search Report and the Written Opinion dated Jul. 24, 2018 From the International Searching Authority Re. Application No. PCT/IL2018/050402. (16 Pages).

Akpinar et al. "Cement Leakage and Complication of Liposarcoma Spinal Metastasis During Vertebral Augmentation Procedure: A Case Report", Journal of Medical Case Reports, 10(1): 40-1-40-4, Dec. 2016.

Lin et al. "Vertebroplasty: Cement Leakage Into the Disc Increases the Risk of New Fracture of Adjacent Vertebral Body", American Journal of Neuroradiology, AJNR, 25(2): 175-180, Feb. 2004.

Mühlebach et al. "New Water-Soluble Photo Crosslinkable Polymers Based on Modified Poly(Vinyl Alcohol)", Journal of Polymer Science, Part A: Polymer Chemistry, 35(16): 36003-3611, Nov. 30, 1997.

Nicholson et al. "Structural and Material Mechanical Properties of Human Vertebral Cancellous Bone", Medicical Engineering and Physics, 19(8): 729-737, Dec. 1997.

Yang et al. "Effective Modulus of the Human Intervertebral Disc and Its Effect on Vertebral Bone Stress", Journal of Biomechanics, 49(7): 1134-1140, May 3, 2016.

Notification of Office Action dated Jun. 2, 2021 From the State Intellectual Property Office of the People's Republic of China Re. Application No. 201880037276.3 and Its Translation Into English. (9 Pages).

Notification of Office Action and Search Report dated Feb. 21, 2022 From the State Intellectual Property Office of the People's Republic of China Re. Application No. 201880037276.3 and Its Translation of Office Action Into English. (11 Pages).

Notification of Office Action and Search Report dated Feb. 21, 2022 From the State Intellectual Property Office of the People's Republic of China Re. Application No. 201880037276.3. (7 Pages).

Notification of Office Action dated Jun. 15, 2022 From the State Intellectual Property Office of the People's Republic of China Re. Application No. 201880037276.3 and Its Translation Into English. (9 Pages).

* cited by examiner

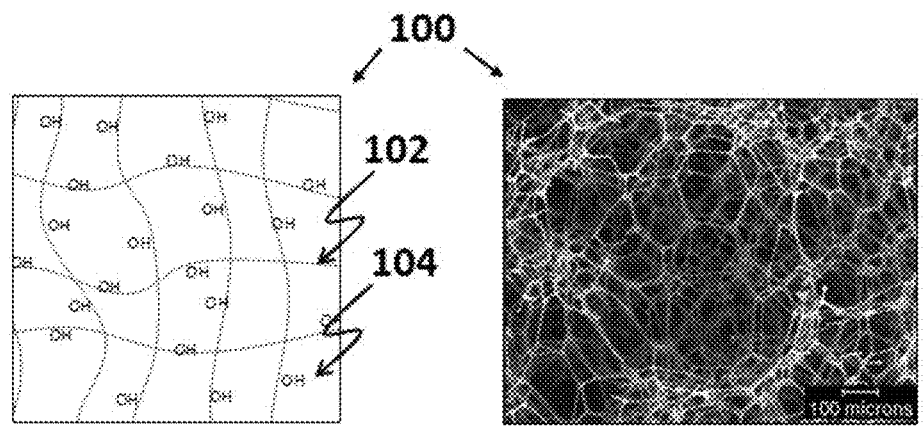
FIGURE 1A  FIGURE 1B
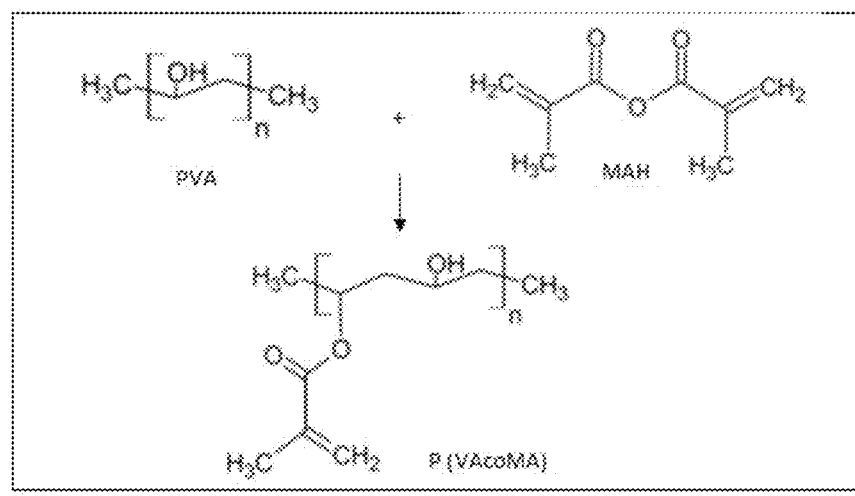
FIGURE 2
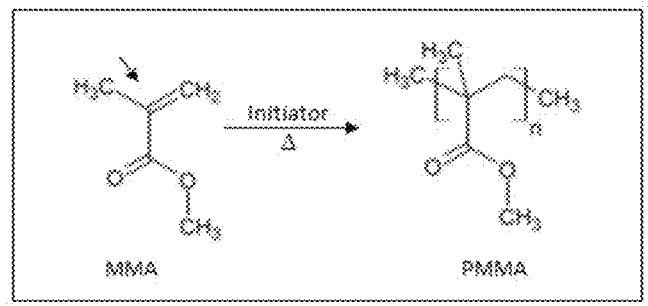
FIGURE 3

PROPERTY CHANGING IMPLANT

RELATED APPLICATIONS

This application is a National Phase of PCT Patent Application No. PCT/IL2018/050402 having International Filing Date of Apr. 4, 2018, which claims the benefit of priority under 35 USC § 119(e) of U.S. Provisional Patent Applications Nos. 62/481,688 filed on Apr. 5, 2017 and 62/530,400 filed on Jul. 10, 2017. The contents of the above applications are all incorporated by reference as if fully set forth herein in their entirety.

FIELD AND BACKGROUND OF THE INVENTION

The present invention, in some embodiments thereof, relates to medical grade and non-medical grade materials which are configured to change their property following stimulation.

Bone fractures are caused by high force impact or stress, where the fracture is then properly termed a traumatic fracture, or as by certain medical conditions that weaken the bones, such as osteoporosis, metastatic bone disease, or osteogenesis imperfecta, where the fracture is then properly termed a pathologic fracture.

A common surgery procedure to treat bone fractions comprises in the use of orthopedic implants for replacing or supplementing or augmentation of the fractured or degenerated bone. Numerous types of biocompatible orthopedic implants are available. Some are made of solid metals, such as stainless steel, cobalt-chromium-molybdenum alloy, tungsten, titanium, cobalt-chromium-tungsten-nickel, and similar alloys. Others are made of solid polymers compounds such as polyetheretherketone (PEEK). Some orthopedic implants are also made of ceramics or composite materials.

Orthopedic implants are available either pre-shaped to their final structure after implant, or expandable implants that enable minimally invasive insertion and then deploy to final form. Implants that are pre-shaped to their final structure, such as nail implants, stem implants and plate implants are in most cases stronger and can be implemented in almost any required shape or size. The main disadvantage of the pre-shaped implants is that in many cases an open surgery is needed in order to position and secure the implant. Open surgery involves large incisions and longer recovery time. Expandable implants such as lumbar expandable cage or stents can be implanted in a minimally invasive procedure that result in less scars and faster recovery time, but the design of the implant is more complicated and the implant structure is limited in shape and size. Both pre-shaped implants and expandable implants that are made from solid, non-elastic parts share one major disadvantage; implants are made in different shapes and sizes, but they have very limited possibility to perfectly adjust to the optimal configuration of each patient anatomy.

One way to apply an implant that will perfectly match the required anatomy and can be implanted via a minimally invasive procedure is by injecting adhesives or cement such as Poly Methyl Methacrylate (PMMA). The PMMA is injected while in a liquid state. The PMMA cement is then cured at the target site resolved in a solid matter that perfectly matches the desired anatomy. This method is widely used in procedures like Vertebroplasty or Kyphoplasty. Although cement injection has many advantages like pain relief and can be done via a minimally invasive procedure, the use of this technique involves a high risk of cement leakage. Extrusion of the injected cement into the vertebral canal may lead to spinal cord or nerve root compression and paralysis.

The use of solid implant together with cement injection, on a single procedure is done occasionally. After placing the solid implant, cement is injected to fill the voids and improve the implant anchoring. This technique requires longer procedure time and still involves a risk of cement leakage. The connection between the cement and implant is based on physical anchoring with no chemical bonding.

In order to benefit the advantage of minimally invasive cement injection while minimizing the risk of leakage, several techniques were developed. These techniques consist of using a meshed balloon that is inserted to the target site e.g. fractured vertebra. Cement is then injected into the meshed balloon, allowing the balloon expansion and deform according to the target anatomy. Some amount of cement leaks throughout the mesh pores, allowing cement leakage to reach undesired areas. Therefore, a non-leaking implant is desired.

US patent application US2016287516A discloses "an improved polymer delivery system which provides polymeric microparticle compositions and porous microparticles formed therefrom. Pore size, pore architecture as well as particle size are also controllable. In some embodiments, both the polymeric microparticle compositions and porous microparticles formed therefrom encapsulate at least one substance, such as a biologic substance (one having biologic activity and/or compatible with a biologic system). The encapsulation occurs prior to polymerization. The amount of substance that is encapsulated may be controlled by the described methods. Said methods do not imply organic solvents. As such, the fabrication occurs in a solvent-free system".

U.S. Pat. No. 6,340,648B discloses "a calcium phosphate porous sintered body which comprises spherical pores communicating with one another substantially throughout the body with a porosity of 55% or more and 90% or less, and has an average diameter of the inter-pore communicating parts of 50 μm or more, a pore diameter of 150 μm or more, and a three-point bending strength of 5 MPa or more, and a method for producing the same".

International patent application WO09087610A2 discloses "a composite material comprising 80%-95% by volume of a solid porous material and 5%-20% by weight of a thermoset polymer, wherein the density of the composite material is 0.11-0.85 gr/ml".

U.S. Pat. No. 6,476,087B discloses "a method of manufacturing syntactic foam which includes the steps of combining a polymer, microspheres and a solvent to form a slurry. At least a portion of the solvent is removed through a porous wick, and conditions are applied which substantially solidify the polymer".

US patent application US2011319510A discloses "a silicone rubber sponge-forming emulsion composition is provided that, even when the quantity of reinforcing silica filler is increased, does not exhibit a decline in emulsion stability, avoids defects in cell morphology of the sponge, and avoids a substantial increase in hardness of the sponge. A method of producing a silicone rubber sponge from this composition is also provided. The A silicone rubber sponge-forming emulsion composition comprises (A) 100 weight parts of a liquid diorganopolysiloxane that has at least two silicon-bonded alkenyl groups in each molecule, (B) 1 to 50 weight parts of a reinforcing silica filler comprising (b1) a fumed silica and (b2) a precipitated silica in a (b1)/(b2) weight ratio of 0.01/1 to 30/1, (C) 50 to 250 weight parts of water that contains (c) a smectite clay, (D) 0.1 to 7 weight parts of a sorbitan fatty acid ester, (E) 0 to 10 weight parts of an isononanoic acid ester, (F) 0 to 10 weight parts of a Guerbet alcohol, and (G) a curing agent in a quantity sufficient to crosslink and cure component (A)".

US patent application US2010075056A discloses "a method for fabricating a porous elastomer, the method comprising the steps of: providing a predetermined amount of a liquid elastomer and a predetermined amount of a porogen; mixing the liquid elastomer and the porogen in vacuum until a homogenous emulsion without phase separation is formed; curing the homogenous emulsion until polymerizations of the emulsion is reached, thereby forming a cured emulsion; and removing the porogen from the cured emulsion. The method can advantageously be used for forming biocompatible porous elastomers and biocompatible porous membranes".

US patent application US2010178488A discloses "a thermoplastic resin foam which excels typically in strength, flexibility, cushioning properties, and strain recovery and is especially resistant to cell structure shrinkage caused by the restoring force of resin. The thermoplastic resin foam which is obtained by subjecting a thermoplastic resin composition containing a thermoplastic elastomer and an active-energy-ray-curable resin to foam molding to give a foamed structure, and irradiating the foamed structure with an active energy ray to allow the active-energy-ray-curable resin to form a cross-linked structure in the foamed structure. Also, the thermoplastic resin foam which is obtained by subjecting a thermoplastic resin composition containing a thermoplastic elastomer, an active-energy-ray-curable resin, and a thermal cross-linking agent to foam molding to give a foamed structure, irradiating the foamed structure with an active energy ray to allow the active-energy-ray-curable resin to form a cross-linked structure in the foamed structure, and heating the resulting foamed structure bearing the cross-linked structure to thereby allow the thermal cross-linking agent to form another cross-linked structure in the foamed structure".

Chinese patent application CN101966409A discloses "a novel macromolecular filter material and a preparation method thereof. The method comprises the following steps of: performing cross-linking curing on polyvinyl alcohol linear macromolecular filter material, foaming auxiliary agent, cross linker and catalyst, performing foaming at the early stage or the medium-late stage of the cross-linking curing link to form porous foam, then further performing cross-linking ageing to obtain sponge matrix, cleaning the sponge matrix, and hardening the sponge matrix; and finally, cleaning and shearing the hardened product to obtain the novel macromolecular filter material. The method can adjust the density and diameter of foam holes in a large range and can load a filter modified material; and the obtained novel macromolecular composite filter material has the advantages of good hydrophilic or lipophilic property, high filter flow rate, strong chemical weather resistance, good mechanical property, wide variable range of technical parameters, reutilization and natural degradability, and can be widely applied in filter treatment processes of industries of beverage, sugar refining, chemical engineering, industrial oil and the like and in the industries of water treatment, air filter and the like".

US patent application US2007129456A discloses "heats to melt a urethane prepolymer (A ingredient) including a hydroxyl (—OH) functional group in a liquid state or a semi-solid state at room temperature as itself or temperature at 30° C. to 80° C., an isocyanate compound (B ingredient) for reacting with a hydroxyl functional group of urethane prepolymer, a mixture (C ingredient) of a hardening catalyst by cross-link, a pores formation assistance catalyst, a silicone surfactant, and an additive is added by fixed quantity and agitation at high speed to mix. Thus formed porous material of cream shape is using by knife coating process. Thus, the purpose of the present invention is manufacturing a solvent-less urethane porous foamed material fabricating synthetic leather as uniformity of micro pores and good mechanical properties of high strength".

US patent application US2013165575A discloses "an artificial marble includes an artificial marble matrix made of a thermosetting resin and metal chips having a cellular structure. The metal chips can be evenly dispersed throughout the artificial marble and can form foam or open-cell patterns".

US patent application US2011275727A discloses "a resin foam which excels in properties such as strength, flexibility, cushioning properties, and strain recovery, particularly has a cell structure resistant to shrinkage caused by the restoring force of the resin, and has a high expansion ratio".

US patent application US20040220672A1 discloses "an orthopedic implant device that is adapted for providing a support structure in spine treatments and other bone treatments".

SUMMARY OF THE INVENTION

An aspect of the present invention relates to a medical grade implant, comprising a deformable body formed of a polymer comprising functional groups capable of cross-linking to form a cross-link; said body provided in a first configuration which is cross-linked to a second configuration upon application of a selected stimuli; wherein said selected stimuli causes said cross-linking of said functional groups.

In some embodiments, said stimuli is the initiator of the cross-link between said first configuration to said second configuration.

In some embodiments, said cross-linking of said functional groups is cross-linking with each other.

In some embodiments, said cross-linking of said functional groups is cross-linking with another material.

In some embodiments, said stimuli is a liquid.

In some embodiments, the quantity of said liquid is from about 3% to about 100% of the total implant weight; and wherein the time required for said liquid to finish 80% of the cross-linking is from about 1 minutes to about 30 minutes.

In some embodiments, said stimuli comprises temperature.

In some embodiments, said temperature is from about 40 degrees Celsius to about 60 degrees Celsius; and wherein the time required for said stimuli to finish 80% of the cross-linking is from about 5 minutes to about 30 minutes.

In some embodiments, said stimuli comprises ultraviolet (UV) radiation.

In some embodiments, the time required for said UV to finish 80% of the cross-linking is from about 2 seconds to about 5 minutes.

In some embodiments, said stimuli is a monomer.

In some embodiments, in said first configuration said implant has an elastic modulus from about 0.01 to about 1 MPa.

In some embodiments, in said second configuration said device has an elastic modulus from about 2 to about 250 MPa.

In some embodiments, said elastic modulus changes from said first configuration to said second configuration by a factor from about 10 to about 1000.

In some embodiments, said body has an open cell structure having a porosity percentage from about 65% to about 85%.

In some embodiments, said open cell structure allows said body to be shrinked by compression.

In some embodiments, said compression is stabilized by dehydratation.

In some embodiments, the stabilized dehydrated body is expandable by hydration.

In some embodiments, said implant is made of biocompatible materials.

In some embodiments, said implant comprises an isolation envelope configured to enclose said implant and avoid leakage of materials from inside said envelope.

In some embodiments, the cross-linking from said first configuration to said second configuration comprises a non-uniform cross-linking of said functional groups with each other.

In some embodiments, the cross-linking from said first configuration to said second configuration comprises a non-uniform change of elastic modulus in said implant.

In some embodiments, the cross-linking from said first configuration to said second configuration comprises a non-uniform cross-linking location within said implant.

In some embodiments, the cross-linking from said first configuration to said second configuration comprises a biocompatible cross-linking process.

In some embodiments, said implant comprises at least one pharmacological agent.

In some embodiments, said functional group is comprised by a pendant group attached to said polymer.

In some embodiments, the polymer has formula I:

[X]*m*[X(-L-Y)]*n*[X—Z-]*p*    Formula I wherein:
m is zero or a positive integer;
n and p are each independently an integer which is at least 1, wherein the
sum of m, n and p is at least 10;
X is a backbone unit which forms a polymeric backbone;
L is absent or is a linking moiety;
Y is said functional group; and
Z is said first cross-link,
wherein L and Y together form said pendant group.

In some embodiments, the polymer comprises a plurality of backbone units having formula II:

—CR1R2-CR3A-    Formula II wherein:
A is selected from the group consisting of a covalent bond, R4, and a linking group, said linking group being selected from the group consisting of —O—, —S—, alkylene, arylene, cycloalkyl, heteralicyclic, amine, sulfate, sulfonate, sulfonyl, sulfoxide, phosphate, phosphonyl, phosphinyl, alkoxy, aryloxy, thioalkoxy, thioaryloxy, azo, sulfonamide, carbonyl, thiocarbonyl, carboxy, carbonyl, thiocarbonyl, urea, thiourea, carbamyl, thiocarbamyl, amide, epoxide, cyanate and amino; and
R1-R4 are each independently selected from the group consisting of hydrogen, alkyl, alkenyl, alkynyl, cycloalkyl, aryl, heteroaryl, heteroalicyclic, amine, halide, sulfate, sulfonate, sulfonyl, sulfoxide, phosphate, phosphoryl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

In some embodiments, said polymer is selected from the group consisting of poly(vinyl alcohol) (PVA), polyvinylamine (PVM), poly(vinyl chloride), a fluoropolymer, a polyester, a polyurethane, a polyurea, a silicone, and copolymers thereof.

In some embodiments, said polymer is selected from the group consisting of poly(vinyl alcohol), poly(vinyl alcohol-co-ethylene), poly(vinyl alcohol-co-vinyl acetate), poly(vinyl alcohol-co-methyl methacrylate), poly(vinyl alcohol-co-vinyl butyral), poly(vinyl alcohol-co-vinyl chloride), a block copolymer of poly(vinyl alcohol) and poly(ethylene oxide), and copolymers thereof.

In some embodiments, an average molecular weight of side chains in said polymer is no more than 50 Da, optionally no more than 25 Da.

In some embodiments, a weight ratio of side chains to backbone in said polymer is no more than 3:1 (side chain: backbone), optionally no more than 1.5:1.

In some embodiments, said first cross-link comprises a residue selected from the group consisting of a formaldehyde residue, a dialdehyde residue, a dicarboxylic acid residue, a diepoxide residue, and a diisocyanate residue.

In some embodiments, an amount of said first cross-link in said polymer is in a range of from 1 cross-link per 100,000 monomeric units of said polymer to 1 cross-link per 100 monomeric units of said polymer.

In some embodiments, an amount of said first cross-link in said polymer is in a range of from 0.2 to 200 cross-links per 1 MDa of said polymer.

In some embodiments, said functional group is capable of cross-linking via polymerization, optionally free radical polymerization and/or anionic polymerization.

In some embodiments, said functional group is selected from the group consisting of acryl, methacryl, cyanoacryl, and vinylsulfonyl.

In some embodiments, said functional group is attached to a backbone unit of said polymer directly or via a linking moiety selected from the group consisting of —CH2-CH(OH)—CH2-O—, —CH2-CH(OH)—CH2-NR5-, —C(=O)—NH—B—O—, and —C(=O)—NH—B—NR6-, wherein B is a substituted or unsubstituted alkylene, and R5 and R6 are each independently selected from the group consisting of hydrogen, alkyl, cycloalkyl, heteroalicyclic, aryl, and heteroaryl.

In some embodiments, an amount of said functional group in said polymer is in a range of from 1 to 30 functional groups per 100 monomeric units of said polymer.

In some embodiments, an amount of said functional group in said polymer is in a range of from 200 to 6,000 functional groups per 1 MDa of said polymer.

In some embodiments, said polymer comprises at least 10 of said functional group per said first cross-link in said polymer.

An aspect of the present invention relates to a method to treat a bone, comprising: delivering at least one medical grade implant to the targeted place in said bone; and stimulating said at least one implant to cause cross-linking the body of said at least one implant from a first configuration to a second configuration; wherein said delivering comprises delivering said implant in a compressed configuration; and wherein said stimulating comprises stimulating said at least one implant to expand in said targeted place.

In some embodiments, said stimulating said implant comprises stimulating to cause cross-linking; said cross-linking does not cause materials to leak outside said implant.

In some embodiments, said delivering an implant comprises delivering said implant in a compressed configuration.

In some embodiments, further comprising uncompressing said implant once located in said targeted place in said bone; and said uncompressing comprises uncompressing to match a hollow space in said targeted place.

An aspect of the present invention relates to medical grade implant system, comprising: an implant comprising a deformable body formed of a polymer comprising functional groups capable of cross-linking to form a cross-link; said body provided in a first configuration which is cross-linked to a second configuration upon application of a selected stimuli; wherein said selected stimuli causes said cross-linking of said functional groups; a medical grade implant delivery device; and at least one stimuli.

An aspect of the present invention relates to a medical grade implant kit, comprising: a biocompatible material comprising at least two interconnected materials, one polymer and at least one cross-linker; and at least one initiator.

An aspect of the present invention relates to a deformable body formed of polymer comprising functional groups capable of cross-linking with each other to form a cross-link, said body provided in a first configuration which is cross-linked to a second configuration upon application of a selected stimuli; wherein said selected stimuli causes said cross-linking of said functional groups with each other.

An aspect of the present invention relates to a non-medical grade implant, comprising a deformable body formed of a polymer comprising functional groups capable of cross-linking to form a cross-link; said body provided in a first configuration which is cross-linked to a second configuration upon application of a selected stimuli; wherein said selected stimuli causes said cross-linking of said functional groups.

An aspect of the present invention relates to the use of a material for medical grade implants comprising a deformable body formed of a polymer comprising functional groups capable of cross-linking to form a cross-link; said body provided in a first configuration which is cross-linked to a second configuration upon application of a selected stimuli; wherein said selected stimuli causes said cross-linking of said functional groups.

In some embodiments, the present invention to provide an implant, a delivery device and a method to treat bone fractures or to strengthen weak bones in order to prevent fracture.

In some embodiments, the present invention to provide an implant and a method for bone augmentation.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is an illustration of a backbone sponge structure, in accordance with some embodiments of the invention;

FIG. 1B is an image of a Polyvinyl alcohol (PVA) sponge, in accordance with some embodiments of the invention;

FIG. 2 is a chemical illustration of substitution of polyvinyl alcohol (PVA) with methyl-methacrylate (MMA) groups, in accordance with some embodiments of the invention;

FIG. 3 is a chemical illustration of polymerization of methyl methacrylate molecules (MMA) to polymethyl methacrylate (PMMA) polymer, in accordance with some embodiments of the invention;

DESCRIPTION OF SPECIFIC EMBODIMENTS OF THE INVENTION

Overview

Figure 4A:
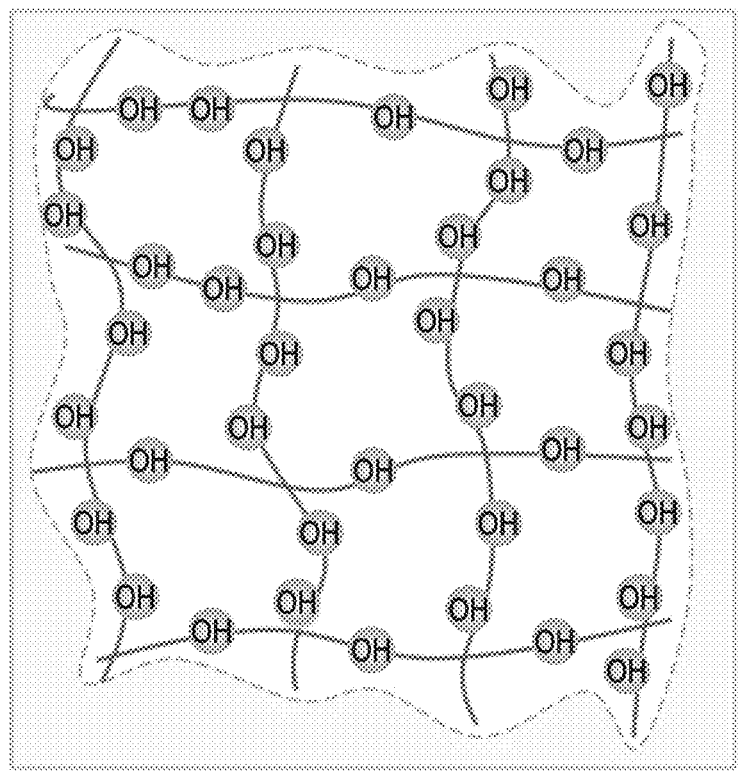
FIG. 4A is an illustration of the structure of PVA sponge, in accordance with some embodiments of the invention.
Figure 4B:
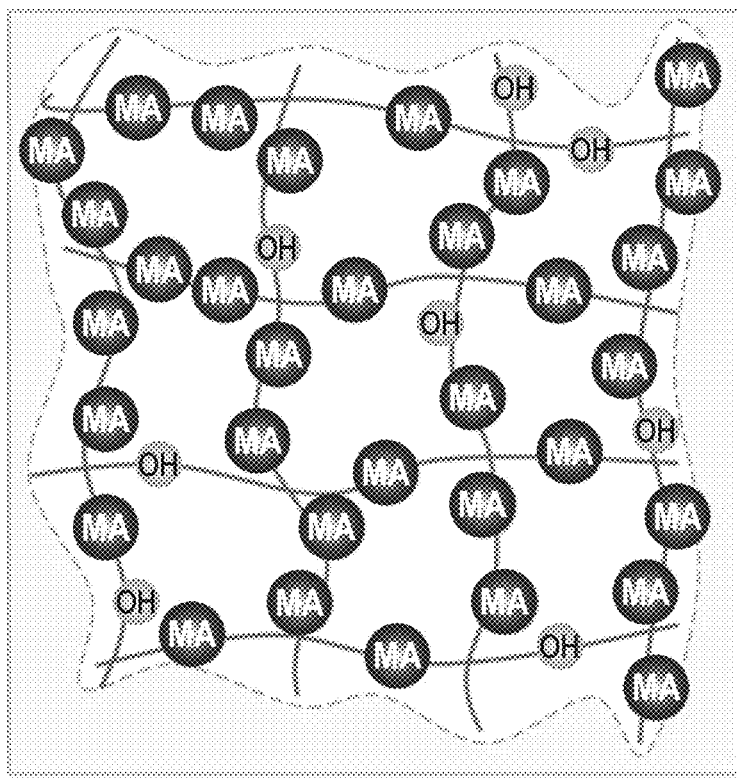
FIG. 4B is an illustration of the structure of the poly (vinyl-alcohol co methacrylate) sponge, in accordance with some embodiments of the invention.

An aspect of some embodiments of the present invention relates to implants capable to be inserted through narrow passages and fill voids larger than the narrow passage.

In some embodiments, the implant comprises several hardening states, from soft to hard. In some embodiments, the changes between hardening states are controllable by the user. In some embodiments, the changes between hardening states are reversible. In some embodiments, the changes between hardening states are irreversible.

In some embodiments, the implant comprises several volumetric states. In some embodiments, the changes between volumetric states are controllable by the user. In some embodiments, the changes between volumetric states are reversible. In some embodiments, the changes between volumetric states are irreversible.

In some embodiments, the implant comprises several states of elasticity. In some embodiments, the changes in the states of elasticity are controlled by the user. In some embodiments, the changes in the states of elasticity are reversible. In some embodiments, the changes in the states of elasticity are irreversible.

In some embodiments, the changes in the variety of states are initiated by a trigger and/or an initiator.

In some embodiments, the implant comprises a sponge structure. In some embodiments, the structure of the implant is configured to allow passage of liquids, bone growth and tissue growth.

In some embodiments, the implant is easily delivered, repositioned and retrieved to/in/from the site.

An aspect of some embodiments of the present invention relates to orthopedic implants comprising at least one type polymer and at least one type of functional group.

In some embodiments, each at least one type of functional group attached to at least one binding site of the at least one type of polymer. In some embodiments, each at least one type of functional group is attached to at least two or at least three binding sites of said at least one type of polymer. In some embodiments, the at least one type of functional group is connected on a first side to the at least one type of polymer, and is connected on a second side to another at least one type of functional group and/or to another at least one type of polymer.

An aspect of the present invention relates to methods to deliver an implant to a specific site in a first configuration, then stimulating the components of the implant to change to a second configuration by a cross-linking process. In some embodiments, the cross-linking process is initiated using a small quantity of stimuli. In some embodiments, the cross-linking process do not enable leakage of materials to the surrounding area where the implant is located. In some embodiment, the cross-linking process comprises a minimal exothermic reaction.

In some embodiments, the orthopedic implant comprises pores. In some embodiments, the size of the pores are from about 1 micron to about 10 millimeters.

In some embodiments, bubbles are present during the reaction of the mixture.

In some embodiments, the orthopedic implant is characterized by a variety of sizes and shapes. In some embodiments, the shapes can be any geometrical form. In some embodiments, the size is from about 1 millimeter square to about 100 centimeter square.

An aspect of some embodiments of the invention relates to an orthopedic implant kit consisting of bone cement and a component having uncured cement absorption property. The present invention also relates to a device designed to contain the implant components and deliver the implant to the target site, optionally, via a minimally invasive procedure. The present invention also relates to a method for efficiently deliver and position the implant.

In some embodiments, an implant, implemented in any desired shape and form, having elastic property and uncured cement absorption property e.g. sponge. The implant is squeezed into a delivery tube. The delivery tube is filled with uncured bone cement. A delivery device consists of the delivery tube and means to eject the implant and bone cement through the delivery tube outlet. While the implant is ejected out of the delivery tube, it expands due to its elastic property. The expanded portion of the implant swells the uncured bone cement due to capillary effect or other effect. In some embodiments, the absorption of the liquid phase, e.g. cement, to the implant occurs due to chemical reactive process. In some embodiments, the absorption of the liquid phase to the implant occurs due to physical process. In some embodiments, the absorption of the liquid phase is done due to both chemical and physical process.

In some embodiments, the implant is first compressed. Optionally, the implant is then dried to stabilize the compression. The compressed implant is placed at the implantation target site and then filled and expanded. The filled and expanded implant is cured to form a solid structure.

In some embodiments, the implant is placed in a delivery tube. In some embodiments, the delivery tube is filled with uncured bone cement. In some embodiments, a delivery device consists of the delivery tube and means to eject the implant and bone cement through the delivery tube outlet. In some embodiments, while the implant is ejected out of the delivery tube, it absorbs the uncured bone cement. In some embodiments, the absorption of the implant with uncured cement causes the implant to expand.

In some embodiments, during an orthopedic procedure e.g. treating fractured bone, the delivery device is inserted to the target site, e.g. a fractured vertebra. In some embodiments, the procedure is optionally done in a minimally invasive procedure, optionally by inserting the delivery tube through a cannula. In some embodiments, the delivery device is then activated to release the implant and the bone cement. In some embodiments, the implant portion that is released out of the delivery tube expands to its pre shape or to the shape forced by the site anatomy. In some embodiments, the implant released out of the delivery device absorbs the uncured cement, optionally, up to a saturated state. In some embodiments, the uncured cement, absorbed in the implant is cured at the target site, forming a solid implant, adapted to the required shape.

In some embodiments, the cement absorbed in the additive material, reduces the risk of cement leakage. In some embodiments, the combination of cement and various types of materials with absorption property may result in improved mechanical properties of the implant and/or to promote bone ingrowth.

In some embodiments, the implant is placed at the target site prior to filling the implant with the liquid material. In some embodiments, only after the implant is placed, the liquid material, e.g. cement, is injected and fills the implant. In some embodiments, the implant is optionally made of a material having high affinity to the liquid injected material and having hydrophobic properties that limit the absorption of body fluids at the implant site.

In some embodiments, the implant serves as a matrix to the liquid filler. In some embodiments, the matrix is optionally selective to the injected liquid, so that it would absorb the injected liquid and repulse water based solution. In some embodiments, for example, for PMMA filler, the implant should attract PMMA by means of functional groups present in the implant, and repulse the water solution of the body tissue. In some embodiments, the implant is optionally made of MMA co polymer or other polymer modified with hydrophobic groups.

In some embodiments, introducing the implant into the target site is done using different techniques. In some embodiments, a compressed implant is injected in parallel to the injection of the liquid filler. In some embodiments, the implant expands and absorbs the liquid filler, thereby preventing leakage of the liquid filler. In some embodiments, the introduction of the implant is done by in-situ cross-linking of two polymers in the injection site. In some embodiments, injection of liquid A and liquid B that, while mixing, produce a solid implant at the desired site. In some embodiments, for example, mixing of diisocyanate and polyol with catalyst, produce a polyurethane implant. In some embodiments, the formation of the foam implant is done by injection of one component and activating the solidification process by ultraviolet light. In some embodiments, the introduction of the implant to the target site is done by in-situ polymerization of the implant. In some embodiments, injection of non-toxic monomers and initiator to the target site, form a solid implant.

In some embodiments, in order to enable adequate absorption of the injected liquid into the implant, the implant is optionally made with open cells. Thus, in some embodiments, the absorbed liquid can flow freely into the implant and fill the empty cavities. In some embodiments, the size, surface and properties of the cells are optionally optimized to attract the filler liquid and keep it inside the implant until cured. In some embodiments, the density and thickness of the cell walls are optionally optimized to, on one hand, increase flexibility and minimize the implant size in a compressed state, and on the other hand, to serve as a strong matrix for the filler while also standing the surrounding forces and the pressure produced by the injected liquid filling.

In some embodiments, the implant is preferably made of a bio-compatible polymer e.g.; poly(methyl acrylate), poly (methyl methacrylate), poly(ethyl methacrylate), polyvinyl-chloride, polytetrafluoroethylene, polyethersulfone, polyethylene, polyetherketone, polysulfone, polypropylene. In some embodiments, a co-polymer is used. In some embodiments, a combination of different polymers or co-polymers or other bio-compatible materials are used.

In some embodiments, the implant is made of a Methacrylic Absorbing Sponge (MAS): a sponge made of polymer with high affinity to methacrylic monomers and oligomers. In some embodiments, releasing pressed MAS in the presence of methacrylic solution, attracts the acrylic molecules and absorbs them. In some embodiments, the absorbing capacity of the MAS can be up to dozen times its own weight depending on the structure of the sponge and the viscosity of the acrylic solution.

In some embodiments, the MAS is made of a polymer composed of two main parts: one part are functional molecules and the other part is a backbone polymer. In some embodiments, the functional molecules have two roles. The first role is to attract the acrylic molecules of the methyl methacrylate (MMA) solution and cause their absorption into the sponge. The second role is to enable chemical binding of the sponge to the absorbed MMA solution during polymerization of the MMA to PMMA, turning the sponge and the PMMA to one substance. In some embodiments, the functional molecules are made of different molecules containing methacrylic or other acrylic side groups. In some embodiments, some of the functional molecules are methyl methacrylate, ethyl methacrylate or other acrylic molecules. In some embodiments, the backbone part role is to serve as a flexible network with a structural and properties of an open-pore sponge enabling the absorption of liquids. In some embodiments, the backbone part is made of long and flexible biocompatible polymer. In some embodiments, some of the backbone polymer is polyvinyl alcohol (PVA) at different percentage of hydrolysis, polyvinyl acetate, co polymers of polyethylene oxide and polypropylene oxide in different ratios or others. In some embodiments, the polymers have different length, molecular weight, and conformation.

In some embodiments, synthesizing the MAS is done by preparation of a network sponge from the backbones molecules, for instance a PVA sponge, having a post modification with functional molecules, for instance esterification of the PVA hydroxylic groups with methacrylic anhydride or by urethane bonding with isocyanatoethyl-methacrylate (IEMA) or by glycidyl methacrylate. In some embodiments, synthesizing the MAS is done by first modifying the backbone polymer with the functional molecules following preparation of a network sponge by crosslinking. In some embodiments, the final product is a poly(vinylalcohol co methylmethacrylate), a co polymer of polyvinyl alcohol and methyl-methacrylate.

In some embodiments, the implant is a metacrylic absorbing matrix (MAM): a low dense matrix made of a polymer with high affinity to methacrylate monomers or oligomers.

In some embodiments, the MAM is made of the same molecules as the MAS but instead a sponge structure it is made as a low density bulk. That is to say, the long backbones polymers, previously modified with the functional side groups, are only slightly cross-linked one to each other. In some embodiments, the result is a floppy material with high affinity to MMA molecules. In some embodiments, the MAM has the ability to absorb MMA solution while swelling. In some embodiments, the MAM can absorb up to dozens times of its own volume without leftover space and become a one stiff bulk with the PMMA after curing. In some embodiments, the MAM can absorb up to one dozen times of its own volume without leftover space and become a one stiff bulk with the PMMA after curing.

In some embodiments, the MAM is optionally prepared by using a chained backbone polymer instead of sponged network polymer. In some embodiments, the chained backboned polymer is modified with the functional groups, following by slightly cross-linking of the modified chains.

In some embodiments, the MAM can be manufactured by modifying long PVA polymers with methacrychloride or glycidyl methacrylate, following by cross-linking with hexamethyl diisocyanate (HDI).

In some embodiments, an implant sponge, containing methacrylic groups is first compressed, dried until hardened and squeezed into a delivery tube. In some embodiments, during an orthopedic procedure e.g. treating fractured bone, the dried compressed sponge is transferred into the implantation target site with the delivery device as described herein. In some embodiments, a non-toxic solution e.g. saline is then injected into the compressed sponge. In some embodiments, the implant sponge is made with open cells, thus, the injected solution can flow freely into the sponge and induce its expansion. In some embodiments, the sponge expands until it fills the void volume of the bone or reaches its final expanded shape.

In some embodiments, after full expansion, a biocompatible solution e.g. saline, containing low concentration of acrylic initiator compounds such as peroxide salt and reacting agent e.g. ammonium persulfate and ferrous and/or tetramethylethylenediamine, is injected into the expanded sponge. In some embodiments, the initiators start a polymerization reaction between the methacrylic side groups of the sponge and turns the soft sponge into a hard and stiff PMMA sponge.

In some embodiments, delivery of an initiator is done using different techniques. In some embodiments, the initiator is injected in parallel to the injection of the liquid filler. In some embodiments, the implant expands and absorbs the liquid filler and the initiator, thereby expanding and commencing the hardening process. In some embodiments, the formation of the foam implant is done by injection of one component and activating the solidification process by ultraviolet light.

In some embodiments, all the methacrylic groups are bounded to the solid sponge therefore preventing any possible leakage of acrylic compounds out of the void volume of the treated site. In some embodiments, the biocompatible solution that is used to expand the sponge and the solution used to initiate the polymerization reaction do not pose a danger in a case of leakage from the treated implantation site. In some embodiments, the initiation solution, containing low concentration of initiators, reacts immediately with the methacrylic sponge. Hence, avoiding any leaking drops containing initiators.

In some embodiments, the final structure of the implant is a stiff PMMA sponge. In some embodiments, the size of the porous and the density of the methacrylic groups on the sponge are optionally optimized to achieve the desired sponge compressibility on one hand, and the required strength of the final, cured stiff sponge, on the other hand.

In some embodiments, the compressed sponge is not delivered by prior injection of a biocompatible solution with polymerization initiators. In some embodiments, a biocompatible solution, e.g. saline containing low concentration of acrylic initiator compounds such as peroxide salt and reacting agent e.g. ammonium persulfate and ferrous is injected directly to the dried compressed sponge to expand the sponge and initiate polymerization.

In some embodiments, the sponge containing the methacrylic groups is not compressed and dried before squeezed into a delivery tube. In some embodiments, the sponge expands back to its final size and/or fills the void once ejected out of the delivery tube at the target implantation site. In some embodiments, a biocompatible solution e.g. saline, containing low concentration of acrylic initiator compounds such as peroxide salt and reacting agent e.g. ammonium persulfate and ferrous and/or tetramethylethylenediamine, is then injected into the expanded sponge. In some embodiments, the initiators start a polymerization reaction between the methacrylic side groups of the sponge and turns the soft sponge into a hard and stiff PMMA sponge.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments, "medical grade" refers to a material which is within the standards of the different countries, international associations, etc. (e.g. FDA, ASTM, ISO, etc.).

General Exemplary Implant

In some embodiments, implants that are curable to a hardened form by application of an initiating solution or energy are disclosed. As will be understood by those of skill in the art, a variety of hardening mechanisms can be utilized, depending upon material selection, including for example, curing that is initiated by saline solutions, water, polymers, cross-linkers, ultraviolet radiation, visible light, infrared radiation, radio frequency radiation, X-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation and the like.

Medical grade implants containing a pre-made or semi pre-made hardenable material, and that are configured to be hardened after placement in a desired in vivo position by application of a cure-initiating liquid or energy, may find advantageous use in a variety of different circumstances. For example and without limitation, such implants can be used in circumstances in which it is desirable for medical personnel to work with a medical implant with no risk of leakage, to work with a medical implant adapted to be accurately placed in the body of the subject and/or to work with a medical implant that do not require time consuming preparations.

In some embodiments, the versatility also allows for a less invasive technique for orthopedic implantation procedures, allows for a greater design flexibility with regard to the implant device, and enables the avoidance or reduction of complications that can arise during a wet out mixing process during Surgery. The embodiments are described primarily by reference to bone devices; however, it is intended that the application be understood to encompass medical devices used in other locations, and non-medical devices used in different scenarios (e.g. construction, arts, etc.) as well.

In some embodiments, the invention relates to a medical grade implant. In some embodiments, the invention relates to a medical grade implant system. In some embodiments, the invention relates to a medical grade implant kit. In some embodiments, the invention relates to a medical grade implant delivery device. In some embodiments, the invention relates to a medical grade biocompatible implant initiator. In some embodiments, the invention relates to materials for non-medical applications. In some embodiments, the invention relates to any combination of the abovementioned.

Exemplary Embodiment of an Implant

In some embodiments, the orthopedic device is configured as a Polyvinyl alcohol (PVA) sponge 100, as shown in FIG. 1A. Optionally, the sponge is used as framework of backbones molecules to be modified with functional molecules/groups. FIG. 1A is a schematic illustration of an example of the structure of a PVA sponge. The illustration shows the carbon chains 102, and OH 104 are the hydroxyl groups that can be replaced with functional groups. FIG. 1B shows a magnification image of a PVA sponge. In some embodiments, the pores diameter is from about 100 microns to about 200 microns. Optionally, in some embodiments, the pores diameter may be any size, smaller or larger than the pores appear on FIG. 1B. In some embodiments, the chains are randomly oriented. In some embodiments, the chains are aligned.

In some embodiments, a methyl methacrylate molecule (MMA) is used as the functional group that will substitute the PVA in the sponge. An example of an optional reaction for substitution of polyvinyl alcohol (PVA) with methyl-methacrylate (MMA) groups, is shown in FIG. 2. In some embodiments, some hydroxylic groups of the PVA nucleophilically attack the carboxyilic carbone of methacrylic anhydride (MAH) molecule, resulting in substitution of the hydroxyl group with methyl-methacrylate to produce the poly(vinyl alcohol co methacrylate): P(VAcoMA).

In some embodiments, the P(VAcoMA) is used to attract the methy-methacrylate solution and cause its absorption into the sponge. In some embodiments, on a later step, the MMA is polymerized to PMMA, as shown in FIG. 3.

Figure 4C:
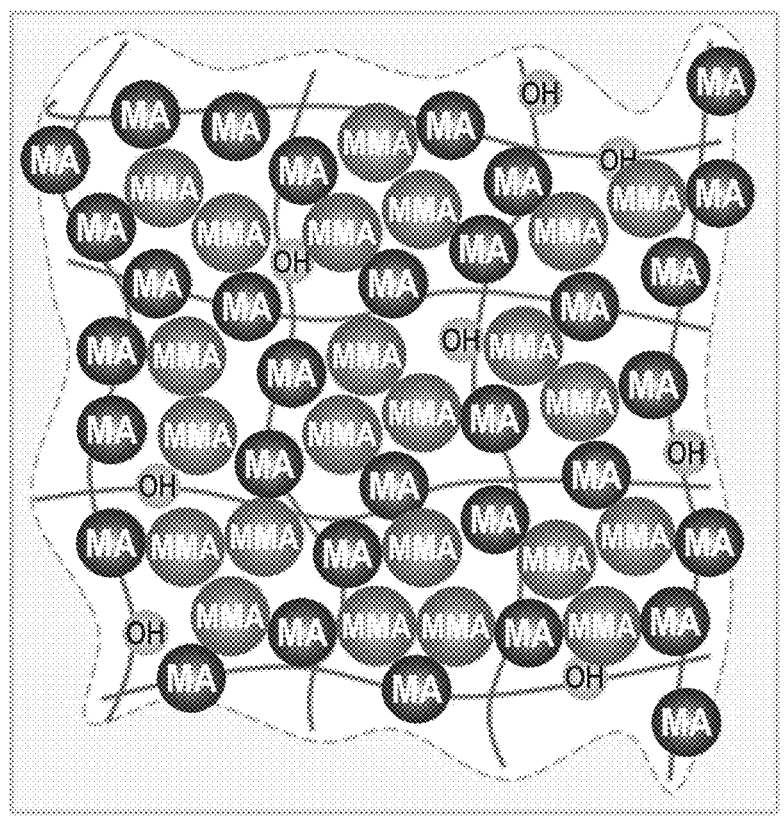
FIG. 4C is an illustration of the P(VAcoMA) sponge after absorbing the MMA solution, in accordance with some embodiments of the invention.
Figure 4D:
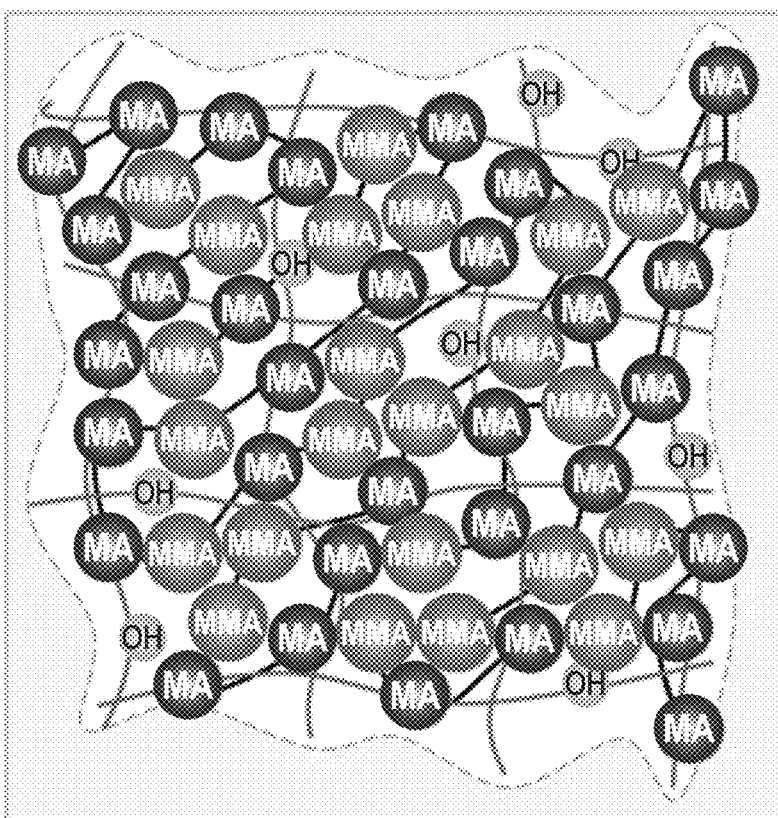
FIG. 4D is an illustration of the MMA absorbed P(VAcoMA) after curing to one PMMA bulk, in accordance with some embodiments of the invention.
Figure 4E:
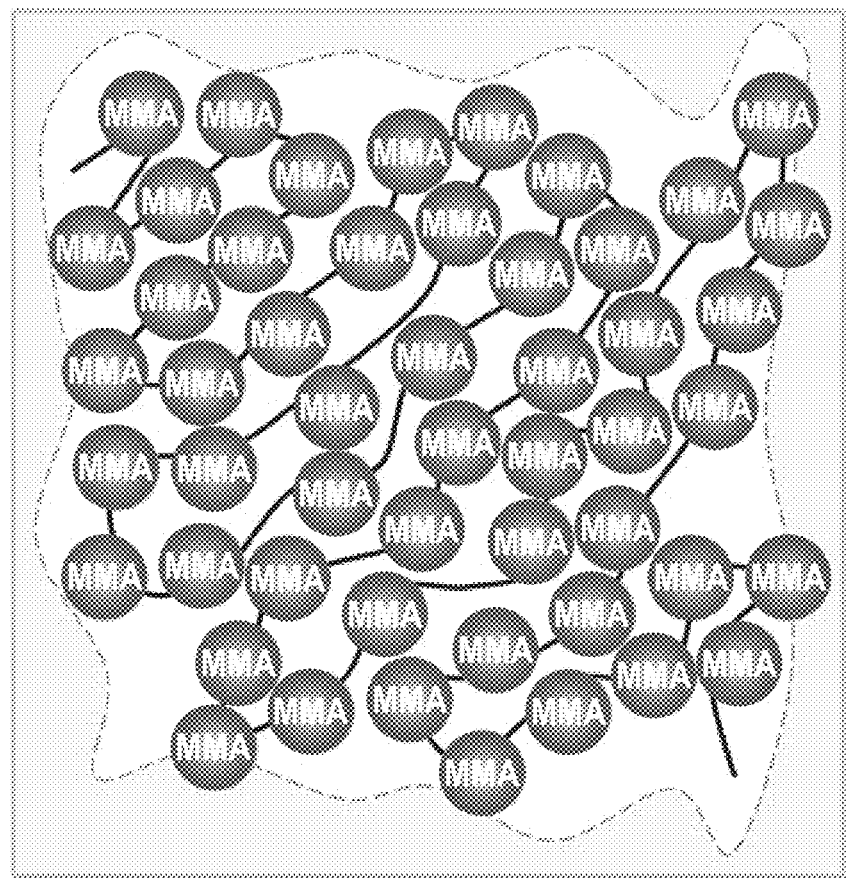
FIG. 4E is an illustration of the PMMA after curing, in accordance with some embodiments of the invention.

In some embodiments, the structural modification and curing process is as depicted, for example, in FIGS. 4A-E. In some embodiments, the structure of the PVA sponge is as illustrated, for example in FIG. 4A. In some embodiments, after the substitution of the polyvinyl alcohol (PVA) with methyl-methacrylate (MMA) groups (Some of the hydroxyls of the PVA were replaced with methacrylate groups), the structure of the poly(vinyl-alcohol co methacrylate) sponge (P(VAcoMA) sponge) is as illustrated, for example in FIG. 4B. In some embodiments, after the P(VAcoMA) sponge absorbs the MMA solution, MMA molecules occupy the spaces in the sponge and are "stuck" to the methacrylic (MA) groups of the sponge, and the structure of the sponge is, for example, as shown in FIG. 4C. In some embodiments, during curing, MMA molecules are covalently bound one to each other and to the MA groups of the sponge resulting in one bulk of PMMA, providing a partial MMA absorbed P(VAcoMA), and the structure of the sponge is, for example, as shown in FIG. 4D. In some embodiments, after all MMA molecules are covalently bonded to each other and to the MA groups and the curing process is completed, the structure of the sponge is, for example, as shown in FIG. 4E.

Figure 5A:
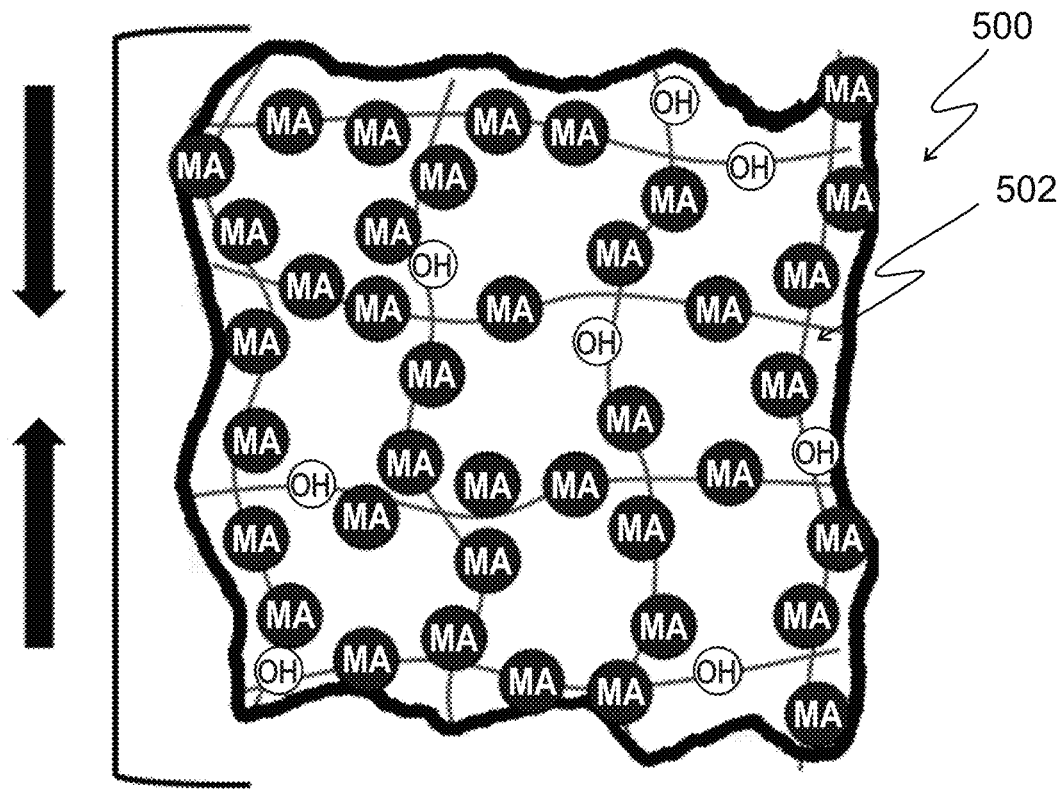
FIG. 5A is an illustration of a non-compressed MMA sponge, in accordance with some embodiments of the invention.
Figure 5B:
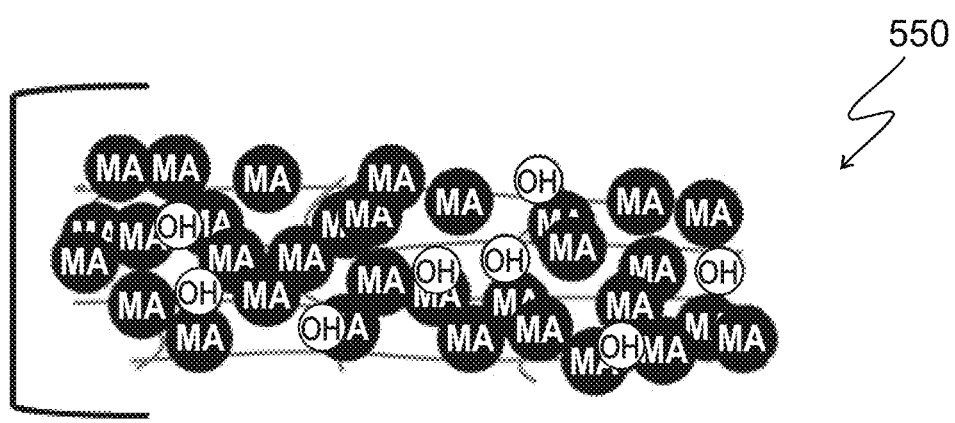
FIG. 5B is an illustration of a compressed MMA sponge, in accordance with some embodiments of the invention.
Figure 5C:
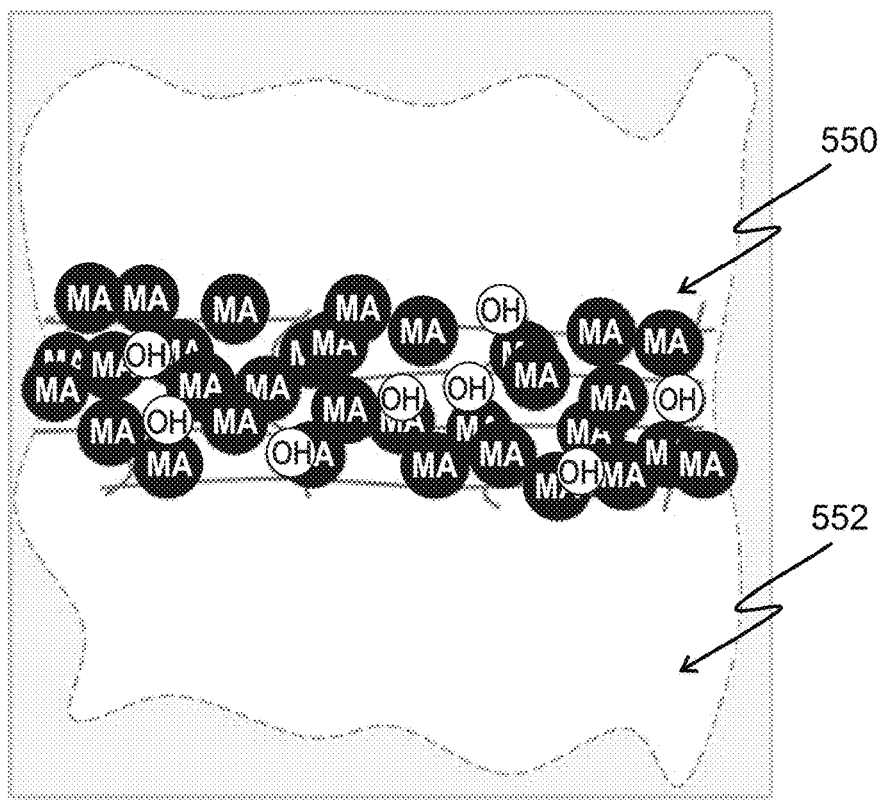
FIG. 5C is an illustration of a compressed MMA sponge, placed at the target implantation void, in accordance with some embodiments of the invention.
Figure 5D:
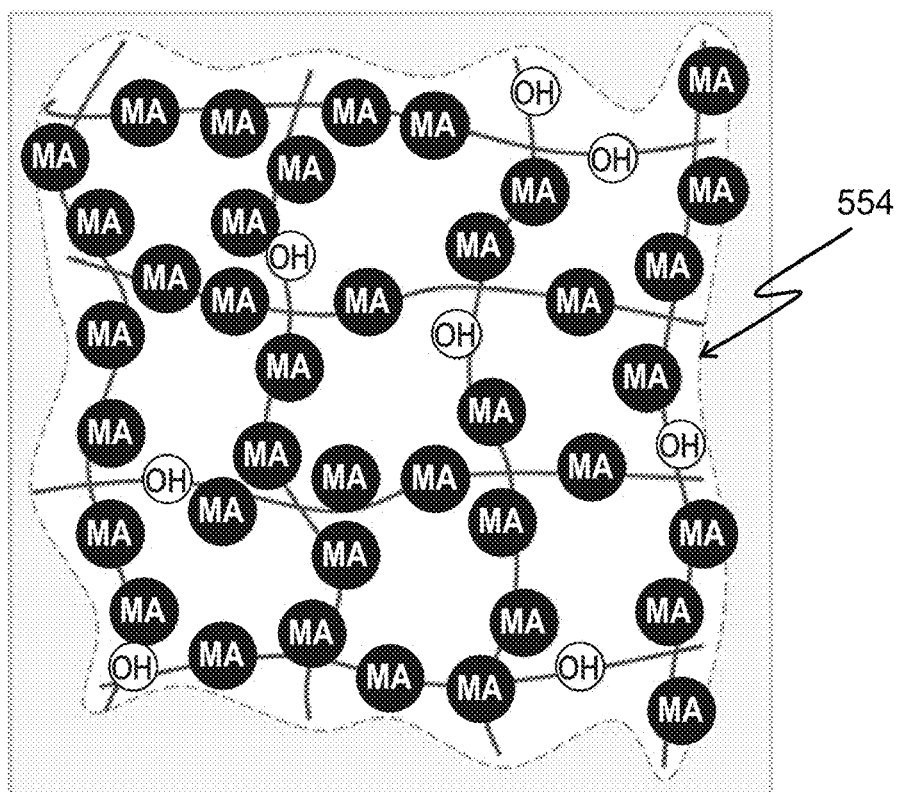
FIG. 5D is an illustration of expanded MMA sponge at the target implantation void, in accordance with some embodiments of the invention.
Figure 5E:
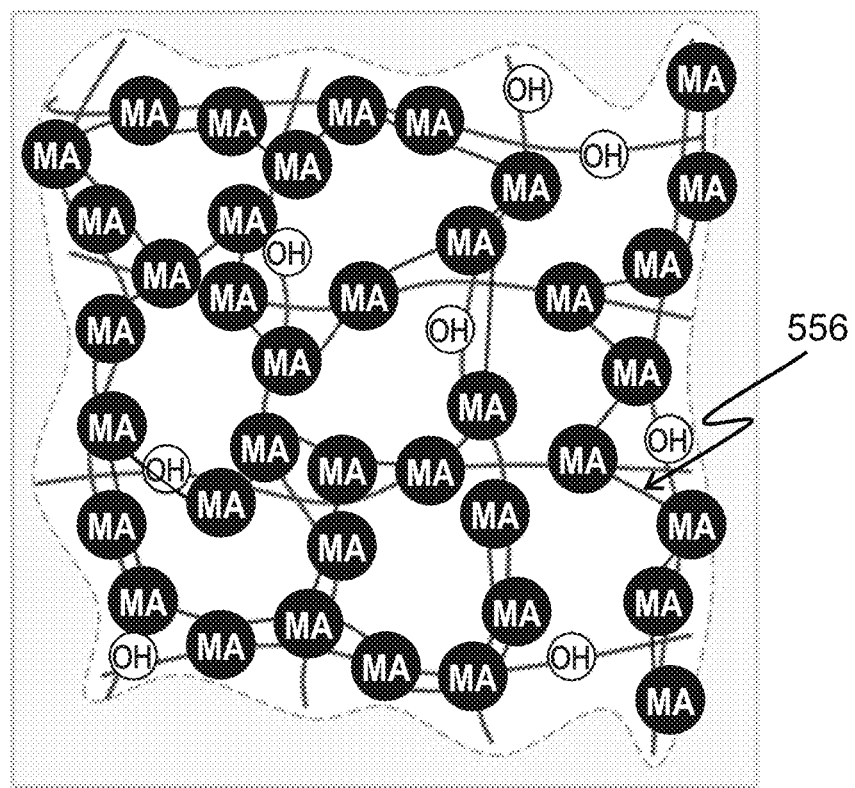
FIG. 5E is an illustration of expanded PMMA sponge, hardened after the injection of initiator solution, injection of initiator solution in accordance with some embodiments of the invention.

In some embodiments, the methacrylate (MA) sponge 500 having a carbon network of PVA 502 is compressed and dried 550 until hardened prior to implantation, as shown for example, in FIGS. 5A-B. In some embodiments, this allows insertion of the implant sponge via a minimally invasive or percutaneous procedure. In some embodiments, the compressed sponge 550 is placed at the target implantation void 552, as shown for example, in FIG. 5C. In some embodiments, once in the implant is in place, a small amount of biocompatible solution (e.g. saline) is injected into the sponge 550, causing the wetted sponge to expand up to its full size or up to the void boundaries 554, as shown for example in FIG. 5D. In some embodiments, once the sponge is expanded, an initiator solution is injected into the expanded sponge generating bonds 556 between methacrylate groups, resulting in a cured hardened polymethacrylate structure, as shown for example, in FIG. 5E.

In some embodiments, the implant comprises a porous architecture which allows the passage of liquids. In some embodiments, the liquids are responsible for hydrating the implant and bring it from a compressed and dried configuration to an expanded configuration. In some embodiments, the liquids are responsible for curating the implant.

In some embodiments, the implant comprises a surface texture that allows the implant to be better embedded in the site of implantation.

In some embodiments, the implant can have a predetermined shape. In some embodiments, the implant is cut to the desired shape using regular tools (e.g. scissors, knifes, etc.). In some embodiments, the implant is expanded inside external molds, and once curated, can be implanted in specific sites. For example, this technique can be used to shape bone plates for skulls or shape specific bone fragments.

Exemplary Compositions of Curable Implant

In some embodiments, a curable implant according to any of the respective embodiments described herein comprises a polymer cross-linked by a first cross-link, the polymer comprising functional groups capable of cross-linking with each other to form a second cross-link (which functional groups are referred to herein interchangeably as "cross-linkable functional groups").

As exemplified in FIGS. 5A-E, curable implants may be obtained using cross-linked PVA as the polymer, with methacrylate functional groups attached to the PVA which are capable of cross-linking with each other (e.g., in the presence of an initiator solution) to form polymerized methacrylate as a second cross-link.

Polymer:

The polymer comprised by the implant (according to any of the respective embodiments described herein) may comprise any suitable polymer known in the art, for example, a biocompatible polymer.

Examples of suitable polymers include, without limitation, poly(vinyl alcohol) (PVA), polyvinylamine (PVM), poly(vinyl chloride), fluoropolymers, polyesters, polyurethanes, polyureas, silicones, and copolymers thereof.

Examples of suitable fluoropolymers include, without limitation, polytetrafluoroethylene (PTFE), poly(vinylidene difluoride) (PVDF), polychlorotrifluoroethylene (PCTFE), and poly(vinyl fluoride) (PVF).

In some embodiments of any of the respective embodiments described herein, the polymer is poly(vinyl alcohol) (PVA) of a copolymer thereof, for example, poly(vinyl alcohol-co-ethylene), poly(vinyl alcohol-co-vinyl acetate), poly(vinyl alcohol-co-methyl methacrylate), poly(vinyl alcohol-co-vinyl butyral), poly(vinyl alcohol-co-vinyl chloride), a block copolymer of poly(vinyl alcohol) and poly(ethylene oxide), or a copolymer thereof (e.g., poly(vinyl alcohol-co-vinyl butyral-co-vinyl acetate) or poly(vinyl alcohol-co-vinyl acetate-co-vinyl chloride), which may be regarded as copolymers of poly(vinyl alcohol-co-vinyl acetate) with poly(vinyl alcohol-co-vinyl butyral) or poly(vinyl alcohol-co-vinyl chloride), respectively).

Thus, for example, the polymer optionally comprises one or more species of backbone units, such as, e.g., vinyl alcohol, vinylamine, vinyl chloride, vinyl fluoride, binylidene difluoride, chlorotrifluoroethylene, ethylene, vinyl acetate, methyl methacrylate, vinyl butyral, and/or ethylene oxide backbone units, as this term is defined herein.

In some embodiments any of the respective embodiments described herein, the polymer has is a cross-linked polymer having formula I:

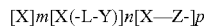 Formula I wherein:

X is a backbone unit which forms a polymeric backbone;

L is absent or is a linking moiety;

Y is a cross-linkable functional group according to any of the respective embodiments described herein;

Z is a first cross-link according to any of the respective embodiments described herein, which attaches to at least two backbone units (only one of which (the X in X—Z) is depicted in formula I;

m is zero or a positive integer, representing an average number of [X] units in a polymeric backbone;

n and p are each independently an integer which is at least 1, representing an average number of [X(-L-Y)] units or [X—Z-] units, respectively, in a polymeric backbone; wherein the sum of m, n and p is at least 10 (optionally at least 100 or at least 1,000, and optionally no more than 1,000,000, no more than 100,000 or no more than 10,000).

As used herein, the term "backbone unit" refers to a repeating unit, which optionally comprises a side chain (as defined herein), wherein linkage of a plurality of the repeating unit (e.g., sequential linkage) forms a polymeric backbone, optionally with side chains attached to the backbone.

Herein, the "backbone" of a polymer refers to a chain of atoms which is formed by linking repeating units (backbone units) to one another to form the polymer, further including hydrogen atoms and oxo groups attached to the chain (whereas other groups attached to the chain of atoms are referred to as side chains).

Herein, the phrase "side chain" refers to any group (comprising one or more atoms) other than a hydrogen atom or oxo (=O), which is attached to an atom in the backbone of a polymer.

As shown in formula I, L and Y together form a pendant group of at least a portion of the backbone units, which group is referred to herein for brevity simply as the "pendant group".

Each backbone unit with a pendant group according to any of the respective embodiments described herein (e.g., a unit represented by X(-L-Y) in formula I, the number of which is represented by the variable n), each backbone unit without a pendant group according to any of the respective embodiments described herein (e.g., a unit represented solely by X in formula I, the number of which is represented by the variable m), and each backbone unit attached to first cross-link according to any of the respective embodiments described herein (e.g., a unit represented by X attached to Z in formula I, the number of which is represented by the variable p), is also referred to herein as a "monomeric unit". Thus, a backbone unit refers to a repeating portion of a monomeric unit, which includes (but is not limited to) the portion which forms a polymeric backbone.

A backbone unit according to any of the respective embodiments described herein may optionally be a residue of a polymerizable monomer or polymerizable moiety of a monomer. A wide variety of polymerizable monomers and moieties will be known to the skilled person, and the structure of the residues of such monomers which result upon polymerization (e.g., monomeric units) will also be known to the skilled person.

A "residue of a polymerizable monomer" refers to a modified form of a polymerizable monomer and/or a portion of a polymerizable monomer that remains after polymerization.

A portion of a polymerizable monomer may be formed, for example, by a condensation reaction, e.g., wherein at least one atom or group (e.g., a hydrogen atom or hydroxyl group) in the monomer, and optionally at least two atoms or groups (e.g., a hydrogen atom and a hydroxyl group) in the monomer, is replaced with a covalent bond with another polymerizable monomer.

A modified form of a polymerizable monomer may be formed, for example, by ring-opening (wherein a covalent bond between two atoms in a ring is broken, and the two atoms optionally each become linked to another polymerizable monomer); and/or by adding to an unsaturated bond, wherein an unsaturated bond between two adjacent atoms is broken (e.g., conversion of an unsaturated double bond to a saturated bond, or conversion of an unsaturated triple bond to an unsaturated double bond) and the two atoms optionally each become linked to another polymerizable monomer.

A modified form of a polymerizable monomer may consist essentially of the same atoms as the original monomer, for example, different merely in the rearrangement of covalent bonds, or alternatively, may have a different atomic composition, for example, wherein polymerization includes a condensation reaction (e.g., as described herein).

A modified form of a polymerizable monomer may optionally be modified following polymerization, for example, by cleavage of a side chain. For example, poly(vinyl alcohol) and copolymers thereof are commonly prepared by polymerizing vinyl acetate (because vinyl alcohol per se is not readily polymerizable) to obtain poly)vinyl acetate) or a copolymer thereof, and then some or all of the acetate groups to obtain vinyl alcohol backbone units (optionally in combination with remaining vinyl acetate backbone units). Vinyl alcohol backbone units may also be formed, for example, by (partial or complete) nucleophilic substitution of a side chain (e.g., chloride in a vinyl chloride unit) by hydroxide.

Examples of backbone units include, without limitation, substituted or unsubstituted hydrocarbons (which may form a substituted or unsubstituted hydrocarbon backbone), such as alkylene units; hydroxycarboxylic acid units (which may form a polyester backbone), e.g., glycolate, lactate, hydroxybutyrate, hydroxyvalerate, hydroxycaproate and hydroxybenzoate units; dicarboxylic acid units (which may form a polyester backbone in combination with a diol and/or a polyamide in combination with a diamine), e.g., adipate, succinate, terephthalate and naphthalene dicarboxylic acid units; diol units (which may form a polyether backbone, or form a polyester backbone in combination with a dicarboxylic acid), e.g., ethylene glycol, 1,2-propanediol, 1,3-propanediol, 1,4-butanediol, and bisphenol A units; diamine units (which may form a polyamide backbone in combination with a dicarboxylic acid), e.g., para-phenylene diamine and alkylene diamines such hexylene diamine; carbamate units (which may form a polyurethane backbone); amino acid residues (which may form a polypeptide backbone); and saccharide residues (which may form a polysaccharide backbone).

In some embodiments of any of the embodiments described herein, the polymer comprises backbone units (e.g., X in formula I) which are a substituted or unsubstituted alkylene unit.

In some embodiments, the polymer comprises backbone units (e.g., X in formula I) which are a substituted or unsubstituted ethylene unit, that is, an alkylene unit 2 atoms in length.

Polymers wherein X is a substituted or unsubstituted ethylene unit may optionally comprise a polymeric backbone such as formed by polymerizing ethylene ($CH_2$=$CH_2$) and/or substituted derivatives thereof (also referred to herein as "vinyl monomers"). Such polymerization is a very well-studied procedure, and one of ordinary skill in the art will be aware of numerous techniques for effecting such polymerization.

It is to be understood that any embodiments described herein relating to a polymers formed by a polymerization encompass any polymers having a structure which can be formed by such polymerization, regardless of whether the polymer was formed in practice by such polymerization (or any other type of polymerization).

As is well known in the art, the unsaturated bond of ethylene and substituted ethylene derivatives becomes saturated upon polymerization, such that the carbon bonds in the polymeric backbone are saturated, although they may be referred to as units of an unsaturated compound (e.g., a "vinyl monomer" or "olefin monomer") to which they are analogous.

Polymers which can be formed from unsaturated monomers such as vinyl monomers and olefin monomers are also referred to by the terms "polyvinyl" and "polyolefin".

Herein, an "unsubstituted" alkylene unit (e.g., ethylene unit) refers to an alkylene unit which does not have any substituent other than the pendant group discussed herein (represented as (-L-Z)). That is, an alkylene unit attached to the aforementioned pendant group is considered unsubstituted if there are no substituents at any other positions on the alkylene unit.

In some embodiments of any of the respective embodiments described herein, the polymer comprises backbone units (e.g., X in formula I) having formula II (wherein $R_1$-$R_3$ and A are as defined herein):

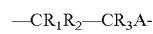  Formula II

When the backbone unit (e.g., X) is not attached to L, Y or Z (i.e., to a pendant group or first cross-link described herein), A is a side chain, such as $R_4$ (as defined herein); and when the backbone unit (e.g., X) is attached to L, Y or Z, A is a covalent bond or a linking group (as defined herein) attaching to L, Y or Z, thus forming a side chain comprising A, L and Y, or A and Z.

When A is a linking group, the linking group may optionally be —O—, —S—, alkylene, arylene, cycloalkyl, heteralicyclic, amine, sulfate, sulfonate, sulfonyl, sulfoxide, phosphate, phosphonyl, phosphinyl, alkoxy, aryloxy, thioalkoxy, thioaryloxy, azo, sulfonamide, carbonyl, thiocarbonyl, carboxy, carbonyl, thiocarbonyl, urea, thiourea, carbamyl, thiocarbamyl, amide, epoxide or amino.

$R_1$-$R_4$ are each independently hydrogen, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine end groups (as defined herein).

Herein, the phrase "linking group" describes a group (e.g., a substituent) that is attached to two or more moieties in the compound.

Herein, the phrase "end group" describes a group (e.g., a substituent) that is attached to a single moiety in the compound via one atom thereof.

When each of $R_1$-$R_3$ is hydrogen, and A is a covalent bond or linking group, the backbone unit (e.g., X) is an unsubstituted ethylene unit attached (via A) to a pendant group or first cross-link described herein.

When each of $R_1$-$R_4$ is hydrogen (and A is $R_4$), the backbone unit (e.g., X) is an unsubstituted ethylene unit which is not attached to a pendant group or first cross-link described herein.

In some embodiments of any of the embodiments described herein, $R_1$ and $R_2$ are each hydrogen. Such embodiments include polymeric backbones formed from many widely used vinyl monomers (including ethylene), including, for example, olefins (e.g., ethylene, propylene, 1-butylene, isobutylene, 4-methyl-1-pentene), vinyl chloride, styrene, vinyl acetate, acrylonitrile, acrylate and derivatives thereof (e.g., acrylate esters, acrylamides), and methacrylate and derivatives thereof (e.g., methacrylate esters, methacrylamides).

In some embodiments of any of the embodiments described herein, $R_3$ is hydrogen. In some such embodiments, $R_1$ and $R_2$ are each hydrogen.

In some embodiments of any of the embodiments described herein, $R_3$ is methyl. In some such embodiments, $R_1$ and $R_2$ are each hydrogen. In some such embodiments, the backbone unit is a unit of methacrylate or a derivative thereof (e.g., methacrylate ester, methacrylamide).

In some embodiments of any of the embodiments described herein relating to formula II, the linking group represented by the variable A is —O—, amine, —C(=O)O—, —C(=O)NH— or phenylene. In exemplary embodiments, A is —O—.

For example, the backbone unit may optionally be a vinyl alcohol derivative (e.g., an ester or ether of a vinyl alcohol unit) when A is —O—; a vinylamine derivative (e.g., an amide or substituted amine of a vinylamine unit) when A is —O— an acrylate or methacrylate derivative (e.g., an ester of an acrylate or methacrylate unit) when A is —C(=O)O—; an acrylamide or methacrylamide unit when A is —C(=O)NH—; and/or a styrene derivative (e.g., a substituted styrene unit) when A is phenylene.

A backbone unit substituted by a pendant group described herein (according to any of the respective embodiments)—e.g., X attached to L-Y in formula I-may be the same as or different than the backbone unit which is not substituted by the pendant group (e.g., X which is not attached to L-Y in formula I, when m is at least 1).

In addition, the plurality of backbone units substituted by a pendant group (according to any of the respective embodiments)—e.g., X attached to L-Y in formula I-may be the same as each other or different from each other.

In addition, the plurality of pendant groups attached to a plurality of backbone units—e.g., L-Y in formula I-may be the same as each other or different from each other (e.g., may differ in the identity of L and/or Y.

In addition, the plurality of backbone units not substituted by a pendant group (according to any of the respective embodiments)—e.g., X which is not attached to L-Y in formula I-may be the same as each other or different from each other. For example, a copolymer described herein may comprise both unsubstituted vinyl alcohol backbone units and additional unsubstituted backbone units (e.g., vinyl acetate, vinyl chloride, etc.), in addition to monomeric units comprising a cross-linkable functional group (e.g., as a substituted vinyl alcohol unit).

The number of types of monomeric units comprising a cross-linkable functional group, the number of types of monomeric units which do not a cross-linkable functional group (if any such units are present), the number of types of backbone units substituted by a pendant group, and/or the number of types of pendant group in the polymer, may each independently be any number (e.g., 1, 2, 3, 4, 5, 6, 7, 8, 9, 10 or more).

In any of the embodiments described herein wherein the polymer comprises two or more types of monomeric units, any two or more different types of monomeric unit (e.g., a unit comprising a cross-linkable functional group and a unit without a cross-linkable functional group; two different types of unit with a cross-linkable functional group; and/or two different types of unit without a cross-linkable functional group) may be distributed randomly or non-randomly throughout the polymer. When different types of monomeric unit are distributed non-randomly, the copolymer may be one characterized by any non-random distribution, for example, an alternating copolymer, a periodic copolymer, and/or a block copolymer.

Cross-Linkable Group:

The cross-linkable groups according to any of the respective embodiments described herein may be any cross-linkable group known in the art, and may be attached to any suitable polymer (according to any of the embodiments described herein in the section relating to the polymer).

In some embodiments of any of the respective embodiments described herein, the cross-linkable functional groups are capable of cross-linking with each other via polymerization (e.g., wherein curing of the implant comprises effecting polymerization), for example, via fee radical polymerization and/or anionic polymerization. Polymerization is optionally effected by contact with a suitable liquid (e.g., an aqueous solution), optionally a solution comprising an initiator (e.g., a free radical initiator, and/or an anionic polymerization initiator such as a nucleophile), and optionally a photoinitiator, which may be activated by illumination (UV and/or visible illumination). In some embodiments, polymerization is inhibited by storage under dry conditions, and initiated by contact with a liquid (e.g., an aqueous solution).

Examples of functional groups cross-linkable via free radical polymerization include, without limitation, acryl ($H_2$=CH—C(=O)—) and methacryl ($H_2$=C(CH$_3$)—C(=O)—) groups. Cyanoacryl ($H_2$=C(C—N)—C(=O)—) is a non-limiting example of a functional group cross-linkable via anionic polymerization.

A wide variety of additional polymerizable functional groups, as well as suitable initiators for each polymerizable functional group, will be known to the skilled person.

Without being bound by any particular theory, it is believed that polymerizable functional groups (e.g., by free radical polymerization) are particularly suitable for cross-linking a substance in vivo, without causing excessive irritation to tissue.

In some embodiments of any of the respective embodiments described herein, at least a portion of the cross-linkable functional groups are comprised by a pendant group attached to the polymer (e.g., a pendant group represented by the variables L and Y in formula I, according to any of the respective embodiments described herein), that is, they form a side chain (wherein the functional group is attached directly to the polymeric backbone) or a portion of a side chain of the polymer (wherein the functional group is attached to the polymeric backbone via one or more linking group, optionally including —O— or —NH—), rather than form the backbone of the polymer. Optionally, the position of a cross-linkable functional group as a pendant group facilitates cross-linking between backbones.

A pendant group (according to any of the respective embodiments described herein) may optionally be attached directly to the polymeric backbone or to a linking group comprised by a backbone unit in the polymer (according to any of the respective embodiments described herein), for example, a linking group represented by A in formula II, according to any to the respective embodiments described herein.

A functional group (according to any of the respective embodiments described herein) may optionally be attached directly to the polymer (e.g., to the polymeric backbone or to a linking group comprised by a backbone unit). Alternatively or additionally, the functional group (according to any of the respective embodiments described herein) is optionally attached to the polymer via a linking moiety, for example, wherein a pendant group comprises the functional group (e.g., Y in formula I) and the linking moiety (e.g., L in formula I), according to any of the respective embodiments described herein. The linking moiety may optionally be attached directly to the polymeric backbone or to a linking group comprised by a backbone unit in the polymer (according to any of the respective embodiments described herein), for example, a linking group represented by A in formula II, according to any to the respective embodiments described herein.

The linking moiety is optionally selected to facilitate attachment of the functional group to the polymer.

Examples of suitable linking moieties include, without limitation, —$CH_2$—CH(OH)—$CH_2$—O—, —$CH_2$—CH(OH)—$CH_2$—$NR_5$—, —C(=O)—NH—B—O—, and —C(=O)—NH—B—$NR_6$—, wherein B is a substituted or unsubstituted alkylene, and $R_5$ and $R_6$ are each independently selected from the group consisting of hydrogen, alkyl, cycloalkyl, heteroalicyclic, aryl, and heteroaryl.

For example, —$CH_2$—CH(OH)—$CH_2$—O— and/or —$CH_2$—CH(OH)—$CH_2$—$NR_5$— are optionally obtained by attaching the functional group or polymer to glycidol (e.g., via an ester, ether, amine or amide linking group), and then attaching the polymer or functional group (respectively) to the epoxide group of glycidol (e.g., via attack by a nucleophilic group, such as hydroxy or amine).

In addition, —C(=O)—NH—B—O—, and —C(=O)—NH—B—$NR_6$— are optionally obtained by attaching the functional group or polymer to a compound comprising an isocyanate group (e.g., via an ester, ether, amine or amide linking group)—for example, a compound having the formula O=C=N—B—OH or O=C=N—B—$NHR_6$—and then attaching the polymer or functional group (respectively) to the isocyanate (e.g., by attack a nucleophilic group, such as hydroxy or amine).

The nature of the second cross-links formed upon cross-linking of the cross-linkable functional groups (e.g., upon curing of the implant) will be understood by the skilled person, in view of any given cross-functional group and in some cases, considering the type of polymer or additional agent present upon cross-linking.

For example, polymerizable functional groups (e.g., acryl, methacryl, cyanoacryl and vinylsulfonyl) will generally form dimeric, trimeric, oligomeric and/or polymeric moieties formed upon polymerization of the polymerizable functional group.

Cross-Links:

The first cross-link may comprise any suitable linking group capable of attaching to two polymeric backbones, preferably by covalent bonds, for example, a residue of a molecule capable of attaching to two different atoms.

The skilled person will be aware of a wide variety of cross-links and cross-linking agents and techniques suitable for forming such cross-links.

In accordance with common practice in the art, cross-links may be characterized as residues of compounds, for example, residues of a cross-linking agents or structurally related similar compound.

Examples of suitable cross-links which may be incorporated in a polymer according to any of the respective embodiments described herein (in combination with cross-linkable functional groups according to any of the respective embodiments described herein) include, without limitation, formaldehyde residues, dialdehyde residues, dicarboxylic acid residues, diepoxide residues, and diisocyanate residues.

Herein, the term "dialdehyde" refers to a molecule having at least two aldehyde groups, as defined herein. Examples of suitable dialdehydes include, without limitation, linear dialdehydes (e.g., HC(=O)—$(CH_2)$k-C(=O)H, wherein k is 0 or a positive integer) such as glyoxal, malondialdehyde, succindialdehyde, and glutaraldehyde; cyclic (e.g., aromatic) dialdehydes such as benzene dicarboxaldehyde (e.g., ortho-phthalaldehyde), naphthalene dicarboxaldehyde, furan dicarboxaldehyde and pyridine dicarboxaldehyde; and macromolecules comprising many aldehyde groups, such as dialdehyde starch (an oxidized derivative of starch, which comprises at least two aldehyde group ion at least a portion of the saccharide residue thereof).

As is known in the art, upon reaction of an aldehyde group with two hydroxyl groups (e.g., adjacent hydroxyl groups in a polymer), an acetal linking group (—CH(—O—)$_2$) is optionally formed, and upon reaction of an aldehyde group with an amine or hydrazine group (as defined herein), an imine or hydrazone linking group (—N=) or hydrazone linking group (—NR—N=), respectively, is optionally formed. Accordingly, a dialdehyde residue may optionally comprise at least two acetal, imine and/or hydrazone linking groups which each attach to a polymeric backbone (e.g., via direct attachment to a backbone carbon atom).

Herein, the term "dicarboxylic acid" refers to a molecule having at least two carboxylic acid groups, as defined herein. Examples of suitable dicarboxylic acids include, without limitation, linear dicarboxylic acids (e.g., HOC(=O)—$(CH_2)$k-C(=O)OH, wherein k is 0 or a positive integer) such as oxalic acid, malonic acid, succinic acid, glutaric acid, adipic acid, pimelic acid, suberic acid, azelaic acid and sebacic acid; and cyclic (e.g., aromatic) dicarboxylic acids such as benzene dicarboxylic acid (phthalate, isophthalate and/or terepthalate), naphthalene dicarboxylic acid, and pyridine dicarboxylic acid (e.g., dipicolinic acid).

As is known in the art, upon reaction of a carboxylic acid group with a hydroxyl group (under suitable conditions), an ester linking group (—C(=O)—O—) is optionally formed, and upon reaction of a carboxylic acid group with an amine group (under suitable conditions), an amide linking group (as defined herein) is optionally formed. Accordingly, a dicarboxylic acid residue may optionally comprise at least two ester and/or amide linking groups which each attach to a polymer backbone (e.g., via direct attachment to a backbone carbon atom).

Herein, the term "diepoxide" refers to a molecule having at least two epoxide groups, as defined herein. Examples of suitable diepoxides include, without limitation, diepoxypropane, diepoxybutane (a.k.a. butadiene diepoxide), diepoxyoctane, and ether diepoxides such as diglycidyl ether.

As is known in the art, upon reaction of an epoxide group with a nucleophilic group (e.g., a hydroxyl or amine group), a hydroxyalkyl linking group (e.g., —CHOH—$CH_2$— or —CH($CH_2$OH)—) is optionally formed. Accordingly, a diepoxide residue may optionally comprise at least two hydroxyalkyl linking groups (e.g., —CHOH—$CH_2$— and/or —CH($CH_2$OH)—) which each attach to a polymer backbone, optionally via a nucleophilic group such as a nitrogen or oxygen atom (e.g., a nitrogen or oxygen atom directly attached to a backbone carbon atom).

Herein, the term "diisocyanate" refers to a molecule having at least two isocyanate groups, as defined herein. Examples of suitable diisocyanates include, without limitation, linear diisocyanates (e.g., O=C=N—$(CH_2)$k-N=C=O, wherein k is 0 or a positive integer) such as hexamethylene diisocyanate; and cyclic (e.g., aromatic) diisocyanates such as phenylene diisocyanate (e.g., para-phenylene diisocyanate), toluene diisocyanate, xylene diisocyanate, naphthalene diisocyanate, isophorone diisocyanate, norbornane diisocyanate, methylene diphenyl diisocyanate, and dibenzyl diisocyanate.

As is known in the art, upon reaction of an isocyanate group with a hydroxyl group, a carbamate linking group (as defined herein) is optionally formed, and upon reaction of an isocyanate group with an amine group, a urea linking group (as defined herein) is optionally formed. Accordingly, a diisocyanate residue may optionally comprise at least two carbamate and/or urea linking groups which each attach to a polymer backbone (e.g., via direct attachment to a backbone carbon atom).

Distribution and Mass of Side Chains and Cross-Links:

As described herein, the properties of the polymer may optionally be controlled by selecting suitable side chains, functional groups and/or first cross-links (according to any of the respective embodiments described herein) and/or suitable proportions thereof.

Without being bound by any particular theory, it is believed that a low proportion of side chains (due to small size of individual side chains and/or to low molar concentration of side chains) facilitates flexibility in the uncured implant by allowing considerable movement of polymeric backbones relative to one another.

In some embodiments of any of the respective embodiments described herein, an average molecular weight of side chains (including first cross-links) in the polymer is no more than 50 Da. In some such embodiments, the average molecular weight is no more than 45 Da. In some embodiments, the average molecular weight is no more than 40 Da. In some embodiments, the average molecular weight is no more than 35 Da. In some embodiments, the average molecular weight is no more than 30 Da. In some embodiments, the average molecular weight is no more than 25 Da. In some embodiments, the average molecular weight is no more than 20 Da.

It is to be appreciated that a low average molecular weight (e.g., according to any of the respective embodiments described herein) may optionally be affected both by low molecular weight of individual side chains (e.g., 17 Da for hydroxyl groups in PVA) as well as by a low proportion of side chains with a higher molecular weight (e.g., functional groups capable of cross-linking with each other, which are optionally large, yet present in only a minority of side chains in the polymer).

In some embodiments of any of the respective embodiments described herein, a weight ratio of side chains to backbone in the polymer is no more than 3:1 (side chain: backbone). In some such embodiments, the weight ratio is no more than 2.5:1 (side chain:backbone). In some embodiments, the weight ratio is no more than 2:1 (side chain: backbone). In some embodiments, the weight ratio is no more than 1.5:1 (side chain:backbone). In some embodiments, the weight ratio is no more than 1:1 (side chain: backbone).

It is to be appreciated that a weight ratio of side chains to backbone (e.g., according to any of the respective embodiments described herein) may optionally be affected both by an average molecular weight of individual side chains (e.g., according to any of the respective embodiments described herein) as well as by a proportion of side chains, for example, whether the polymer comprises one side chain per monomeric unit (e.g., as in monosubstituted vinyl residues such as vinyl alcohol, vinylamine, vinyl acetate and vinyl chloride residues) or multiple side chains per monomeric unit (e.g., as in tetrafluoroethylene or vinylidene difluoride residues).

Without being bound by any particular theory, it is believed that a relatively low proportion of first cross-link in the uncured implant is suitable for maintaining integrity of the implant (e.g., by inhibiting dissolution) while allowing flexibility of the uncured polymer.

In some embodiments of any of the respective embodiments described herein, an amount of the first cross-link (according to any of the respective embodiments described herein) in the polymer is at least 1 cross-link per 100,000 monomeric units, optionally at least 1 cross-link per 30,000 monomeric units, optionally at least 1 cross-link per 10,000 monomeric units, optionally at least 1 cross-link per 3,000 monomeric units, and optionally at least about 1 cross-link per 1,000 monomeric units.

In some embodiments of any of the respective embodiments described herein, an amount of the first cross-link (according to any of the respective embodiments described herein) in the polymer is at least 0.2 cross-links per 1 MDa of the polymer (i.e., at least 1 cross-link per 5 MDa), optionally at least 0.5 cross-links per 1 MDa of the polymer, optionally at least 2 cross-links per 1 MDa of the polymer, optionally at least 5 cross-links per 1 MDa of the polymer, and optionally at least 20 cross-links per 1 MDa of the polymer.

In some embodiments of any of the respective embodiments described herein, an amount of the first cross-link (according to any of the respective embodiments described herein) in the polymer is no more than 1 cross-link per 100 monomeric units of the polymer, for example, in a range of from 1 cross-link per 100,000 monomeric units to 1 cross-link per 100 monomeric units, from 1 cross-link per 30,000 monomeric units to 1 cross-link per 100 monomeric units, from 1 cross-link per 10,000 monomeric units to 1 cross-link per 100 monomeric units, from 1 cross-link per 3,000 monomeric units to 1 cross-link per 100 monomeric units, from 1 cross-link per 1,000 monomeric units to 1 cross-link per 100 monomeric units, or about 1 cross-link per 1,000 monomeric units.

In some embodiments of any of the respective embodiments described herein, an amount of the first cross-link (according to any of the respective embodiments described herein) in the polymer is no more than 1 cross-link per 300 monomeric units of the polymer, for example, in a range of from 1 cross-link per 100,000 monomeric units to 1 cross-link per 300 monomeric units, from 1 cross-link per 30,000 monomeric units to 1 cross-link per 300 monomeric units, from 1 cross-link per 10,000 monomeric units to 1 cross-link per 300 monomeric units, from 1 cross-link per 3,000 monomeric units to 1 cross-link per 300 monomeric units, or from 1 cross-link per 1,000 monomeric units to 1 cross-link per 300 monomeric units.

In some embodiments of any of the respective embodiments described herein, an amount of the first cross-link (according to any of the respective embodiments described herein) in the polymer is no more than 1 cross-link per 1,000 monomeric units of the polymer, for example, in a range of from 1 cross-link per 100,000 monomeric units to 1 cross-link per 1,000 monomeric units, from 1 cross-link per 30,000 monomeric units to 1 cross-link per 1,000 monomeric units, from 1 cross-link per 10,000 monomeric units to 1 cross-link per 1,000 monomeric units, or from 1 cross-link per 3,000 monomeric units to 1 cross-link per 1,000 monomeric units.

Regarding a polymer of formula I (according to any of the respective embodiments described herein), it is noted that the number of first cross-links per 1,000 monomeric units of the polymer is determined by $1,000*p/(m+n+p)$.

In some embodiments of any of the respective embodiments described herein, an amount of the first cross-link (according to any of the respective embodiments described herein) in the polymer is no more than 200 cross-links per 1 MDa of the polymer, for example, in a range of from 0.2 to 200 cross-links per 1 MDa of the polymer (i.e., from 1 cross-link per 5 MDa to 1 cross-link per 5 kDa), from 0.5 to 200 cross-links per 1 MDa of the polymer, from 2 to 200 cross-links per 1 MDa of the polymer, from 5 to 200 cross-links per 1 MDa of the polymer, from 20 to 200 cross-links per 1 MDa of the polymer, or about 20 cross-links per 1 MDa of the polymer.

In some embodiments of any of the respective embodiments described herein, an amount of the first cross-link (according to any of the respective embodiments described herein) in the polymer is no more than 50 cross-links per 1 MDa of the polymer, for example, in a range of from 0.2 to 50 cross-links per 1 MDa of the polymer, from 0.5 to 50 cross-links per 1 MDa of the polymer, from 2 to 50 cross-links per 1 MDa of the polymer, from 5 to 50 cross-links per 1 MDa of the polymer, or from 20 to 50 cross-links per 1 MDa of the polymer.

In some embodiments of any of the respective embodiments described herein, an amount of the first cross-link (according to any of the respective embodiments described herein) in the polymer is no more than 20 cross-links per 1 MDa of the polymer, for example, in a range of from 0.2 to 20 cross-links per 1 MDa of the polymer, from 0.5 to 20 cross-links per 1 MDa of the polymer, from 2 to 20 cross-links per 1 MDa of the polymer, or from 5 to 20 cross-links per 1 MDa of the polymer.

In some embodiments of any of the respective embodiments described herein, an amount of cross-linkable functional groups is greater than an amount of first cross-links, that is, the polymer comprises more than 1 cross-linkable functional group per first cross-link in the polymer.

Without being bound by any particular theory, it is believed that such a difference in the amount of first cross-links and second cross-links is associated with a considerable change in physical properties upon curing, e.g., because of the proportionally large increase in the number of cross-links in the polymer.

In some embodiments of any of the respective embodiments described herein, the polymer comprises at least 3 cross-linkable functional groups per first cross-link in the polymer. In some embodiments, the polymer comprises at least 10 cross-linkable functional groups per first cross-link. In some embodiments, the polymer comprises at least 30 cross-linkable functional groups per first cross-link. In some embodiments, the polymer comprises at least 100 cross-linkable functional groups per first cross-link. In some embodiments, the polymer comprises at least 300 cross-linkable functional groups per first cross-link. In some embodiments, the polymer comprises no more than 10,000, or no more than 1,000 cross-linkable functional groups per first cross-link, for example, from 10 to 1,000 functional groups per first cross-link, or from 30 to 300 functional groups per first cross-link.

Regarding a polymer of formula I (according to any of the respective embodiments described herein), it is noted that the number of cross-linkable functional groups per first cross-link is determined by n/p.

In some embodiments of any of the respective embodiments described herein, the polymer comprises less cross-linkable functional groups than monomeric units, that is, only a portion of the monomeric units of the polymer comprise a cross-linkable functional group. The other monomeric units may optionally lack a side chain (e.g., ethylene residues) or comprise a small side chain (e.g., —OH, —NH$_2$, halo), which is optionally selected for providing a flexible uncured polymer (e.g., as described herein).

Without being bound by any particular theory, it is believed that a presence of cross-linkable functional groups on only a portion of monomeric units in a polymer is associated with increased flexibility, because of either one of the following mechanisms:

a) The cross-linkable functional groups may be sufficiently large to promote rigidity (e.g., by inhibiting backbone movement) if present in excessively large proportions, e.g., if present in each or almost each monomeric unit.

b) Monomeric units comprising cross-linkable functional groups interspersed with other monomeric units in the form of a copolymer (e.g., a random copolymer) may reduce a degree of crystallinity in the polymer (e.g., by reducing repeatability in the polymer sequence), which may be an important cause of rigidity in some polymers, especially polymers with small side chains.

In some embodiments of any of the respective embodiments described herein, an amount of cross-linkable functional group (according to any of the respective embodiments described herein) in the polymer is no more than 50 cross-linkable functional groups per 100 monomeric units of the polymer, optionally no more than 40 cross-linkable functional groups per 100 monomeric units, optionally no more than 30 cross-linkable functional groups per 100 monomeric units, optionally no more than 25 cross-linkable functional groups per 100 monomeric units, optionally no more than 20 cross-linkable functional groups per 100 monomeric units, optionally no more than 15 cross-linkable functional groups per 100 monomeric units, optionally no more than 10 cross-linkable functional groups per 100 monomeric units, and optionally no more than 5 cross-linkable functional groups per 100 monomeric units.

Regarding a polymer of formula I (according to any of the respective embodiments described herein), it is noted that the number of cross-linkable functional groups per 100 monomeric units of the polymer is determined by $100*n/(m+n+p)$.

In some embodiments of any of the respective embodiments described herein, an amount of cross-linkable functional group (according to any of the respective embodiments described herein) in the polymer is at least 1 cross-linkable functional groups per 100 monomeric units of the polymer, for example, from 1 to 30, from 1 to 25, from 1 to 20, from 1 to 15, from 1 to 10, or from 1 to 5 cross-linkable functional groups per 100 monomeric units. In some embodiments, an amount of cross-linkable functional group in the polymer is at least 3 cross-linkable functional groups per 100 monomeric units of the polymer, for example, from 3 to 30, from 3 to 25, from 3 to 20, from 3 to 15, or from 3 to 10 cross-linkable functional groups per 100 monomeric units. In some embodiments, an amount of cross-linkable functional group in the polymer is at least 10 cross-linkable functional groups per 100 monomeric units of the polymer, for example, from 10 to 30, from 10 to 25, from 10 to 20, or from 10 to 15 cross-linkable functional groups per 100 monomeric units. In some embodiments, an amount of cross-linkable functional group in the polymer is about 10 cross-linkable functional groups per 100 monomeric units.

Alternatively or additionally, the proportion of cross-linkable functional groups in the polymer is determined relative to the molecular weight of the polymer (including the functional groups thereof).

In some embodiments of any of the respective embodiments described herein, an amount of cross-linkable functional group (according to any of the respective embodiments described herein) in the polymer is no more than 6,000 cross-linkable functional groups per 1 MDa of the polymer (i.e., 6 groups per 1 kDa), optionally no more than 4,000 cross-linkable functional groups per 1 MDa of the polymer, optionally no more than 2,000 cross-linkable functional groups per 1 MDa of the polymer, optionally no more than 1,000 cross-linkable functional groups per 1 MDa of the polymer, optionally no more than 600 cross-linkable functional groups per 1 MDa of the polymer, optionally no more than 400 cross-linkable functional groups per 1 MDa of the polymer, and optionally no more than 200 cross-linkable functional groups per 1 MDa of the polymer.

In some embodiments of any of the respective embodiments described herein, an amount of cross-linkable functional group (according to any of the respective embodiments described herein) in the polymer is at least 200 cross-linkable functional groups per 1 MDa of the polymer, for example, from 200 to 6,000, from 200 to 4,000, from 200 to 2,000, from 200 to 1,000, from 200 to 600, or from 200 to 400 cross-linkable functional groups per 1 MDa of the polymer. In some embodiments, an amount of cross-linkable functional group in the polymer is at least 400 cross-linkable functional groups per 1 MDa of the polymer, for example, from 400 to 6,000, from 400 to 4,000, from 400 to 2,000, or from 400 to 1,000 cross-linkable functional groups per 1 MDa. In some embodiments, an amount of cross-linkable functional group in the polymer is at least 600 cross-linkable functional groups per 1 MDa of the polymer, for example, from 600 to 6,000, from 600 to 4,000, from 600 to 2,000, or from 600 to 1,000 cross-linkable functional groups per 1 MDa. In some embodiments, an amount of cross-linkable functional group in the polymer is at least 1,000 cross-linkable functional groups per 1 MDa of the polymer, for example, from 1,000 to 6,000, from 1,000 to 4,000, from 1,000 to 2,000, or about 2,000 cross-linkable functional groups per 1 MDa.

Herein, the term "hydrocarbon" describes an organic moiety that includes, as its basic skeleton, a chain of carbon atoms, substituted mainly by hydrogen atoms. The hydrocarbon can be saturated or non-saturated, be comprised of aliphatic, alicyclic or aromatic moieties, and can optionally be substituted by one or more substituents (other than hydrogen). A substituted hydrocarbon may have one or more substituents, whereby each substituent group can independently be, for example, cycloalkyl, alkenyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, oxo, cyano, nitro, azo, azide, sulfonamide, carbonyl, thiocarbonyl, carboxy, thiocarbamate, urea, thiourea, carbamate, amide, epoxide and hydrazine. The hydrocarbon can be an end group or a linking group, as these terms are defined herein.

Preferably, the hydrocarbon moiety has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms.

Herein, the term "alkyl" describes a saturated aliphatic hydrocarbon end group, as defined herein, including straight chain and branched chain groups. Preferably, the alkyl group has 1 to 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, cycloalkyl, alkenyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

The term "alkylene" describes a saturated or unsaturated aliphatic hydrocarbon linking group, as this term is defined herein, which differs from an alkyl group (when saturated) or an alkenyl or alkynyl group (when unsaturated), as defined herein, only in that alkylene is a linking group rather than an end group.

Herein, the term "alkenyl" describes an unsaturated aliphatic hydrocarbon end group which comprises at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or unsubstituted. Substituted alkenyl may have one or more substituents, whereby each substituent group can independently be, for example, cycloalkyl, alkynyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

Herein, the term "alkynyl" describes an unsaturated aliphatic hydrocarbon end group which comprises at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or unsubstituted. Substituted alkynyl may have one or more substituents, whereby each substituent group can independently be, for example, cycloalkyl, alkenyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) end group (as this term is defined herein) having a completely conjugated pi-electron system. The aryl group may be substituted or unsubstituted. Substituted aryl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. Phenyl and naphthyl are representative aryl end groups.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy end group and a —NRx— linking group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring. A carbon atom attached to the nitrogen atom of an amine is not substituted by =O or =S, and in some embodiments, is not substituted by any heteroatom.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "hydroxy" and "hydroxyl" describe a —OH group.

The term "alkoxy" describes both an —O-alkyl and an —O-cycloalkyl end group, or —O— alkylene or —O-cycloalkyl linking group, as defined herein.

The term "aryloxy" describes both an —O-aryl and an —O-heteroaryl end group, or an —O-arylene- linking group, as defined herein.

The term "thiohydroxy" describes a —SH group.

The term "thioalkoxy" describes both an —S-alkyl and an —S-cycloalkyl end group, or —S— alkylene or —S-cycloalkyl linking group, as defined herein.

The term "thioaryloxy" describes both an —S-aryl and an —S-heteroaryl end group, or an —S-arylene- linking group, as defined herein.

The terms "cyano" and "nitrile" describe a —C≡N group.

The term "nitro" describes an —NO$_2$ group.

The term "oxo" describes a =O group.

The term "azide" describes an —N=N+=N$^-$ group.

The term "azo" describes an —N=N—Rx end group or —N=N— linking group, with Rx as defined herein.

The terms "halide" and "halo" refer to fluorine, chlorine, bromine or iodine.

The term "phosphate" refers to a —O—P(=O)(OR$_X$)—OR$_Y$ end group, or to a —O—P(=O)(OR$_X$)—O— linking group, where R$_X$ and R$_Y$ are as defined herein, except when referring to a phosphate ion salt such as a calcium phosphate.

The terms "phosphonyl" and "phosphonate" refer to an —P(=O)(OR$_X$)—OR$_Y$ end group, or to a —P(=O)(OR$_X$)—O— linking group, where R$_X$ and R$_Y$ are as defined herein.

The term "phosphinyl" refers to a —PR$_X$R$_Y$ group, where R$_X$ and R$_Y$ are as defined hereinabove.

The term "sulfoxide" or "sulfinyl" describes a —S(=O)—R$_X$ end group or —S(=O)— linking group, where R$_X$ is as defined herein.

The term "sulfonyl" describe a —S(=O)$_2$—R$_X$ end group or —S(=O)$_2$— linking group, where R$_X$ is as defined herein.

The term "sulfonate" describes a —S(=O)$_2$—O—R$_X$ or —O—S(=O)$_2$—R$_X$ end group or —S(=O)$_2$—O-linking group, where R$_X$ is as defined herein.

The term "sulfate" describes a —O—S(=O)$_2$—O—R$_X$ end group or —O—S(=O)$_2$—O— linking group, where R$_X$ is as defined herein.

The terms "sulfonamide" and "sulfonamido", as used herein, encompass both S-sulfonamide and N-sulfonamide end groups, and a —S(=O)$_2$—NR$_X$— linking group.

The term "S-sulfonamide" describes a —S(=O)$_2$—NR$_X$R$_Y$ end group, with Rx and Ry as defined herein.

The term "N-sulfonamide" describes an R$_X$S(=O)$_2$—NR$_Y$— end group, where Rx and Ry are as defined herein.

The term "carbonyl" as used herein, describes a —C(=O)—R$_X$ end group or —C(=O)— linking group, with R$_X$ as defined herein. The term "aldehyde" herein describes a —C(=O)H end group.

The term "thiocarbonyl" as used herein, describes a —C(=S)—$R_X$ end group or —C(=S)— linking group, with $R_X$ as defined herein.

The terms "carboxy" and "carboxyl", as used herein, encompasses both C-carboxy and O-carboxy end groups, and a —C(=O)—O— linking group.

The term "C-carboxy" describes a —C(=O)—$OR_X$ end group, where Rx is as defined herein. The term "carboxylic acid" describes a —C(=O)—OH end group, or a deprotonated form (—$CO_2^-$) or salt thereof.

The term "O-carboxy" describes a —OC(=O)—$R_X$ end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The terms "amide" and "amido", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes a RyOC(=O)—NRx- end group, with Rx and Ry as defined herein.

The term "O-carbamate" describes an —OC(=O)—NRxRy end group, with Rx and Ry as defined herein.

The term "thiocarbamyl" or "thiocarbamate", as used herein, encompasses O-thiocarbamate, S-thiocarbamate and N-thiocarbamate end groups, and a —OC(=S)—NRx- or —SC(=O)—NRx- linking group.

The terms "O-thiocarbamate" and "O-thiocarbamyl" describe a —OC(=S)—NRxRy end group, with Rx and Ry as defined herein.

The terms "S-thiocarbamate" and "S-thiocarbamyl" describe a —SC(=O)—NRxRy end group, with Rx and Ry as defined herein.

The terms "N-thiocarbamate" and "N-thiocarbamyl" describe a RyOC(=S)NRx- or RySC(=O)NRx- end group, with Rx and Ry as defined herein.

The term "hydrazine", as used herein, describes a —NRx-NRyRw end group or —NRx-NRy- linking group, with Rx, Ry, and Rw as defined herein.

The term "isocyanate", as used herein, describes a —N=C=O group.

As used herein, the term "epoxide" describes a

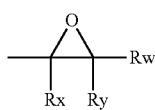

end group or a

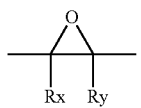

linking group, as these phrases are defined herein, where Rx, Ry and Rw are as defined herein.

Additional Cross-Linking Agents

As described herein, the curable implant comprises, in some embodiments, a modified polymer comprising cross-linkable functional groups. The implant may therefore optionally be cured by cross-linking the cross-linkable functional groups of the polymer per se. Alternatively, one or more additional cross-linking agents may be added to the implant, for example, shortly before or during curing (e.g., as part of a solution injected into the implant), such that the polymer becomes cross-linked by both the cross-linkable functional groups of the polymer and the additional cross-linking agent.

The additional cross-linking agent(s) may comprise any suitable cross-linking agent known in the art. The skilled person will understand which cross-linking agents are suitable for cross-linking any given modified polymer, considering the functionalities of the modified polymer.

The additional cross-linking agent may comprise, for example, a polymerizable monomer as defined herein (e.g., according to any of the respective embodiments described herein). The polymerizable monomer(s) may optionally be a monomer from which at least a portion of the monomeric units of the polymer of the implant are derived (e.g., a vinyl monomer in embodiments wherein the polymer comprises vinyl derivatives as monomeric units), and/or a monomer corresponding to the cross-linkable functional group (e.g., a methacrylate monomer such as methyl methacrylate, in embodiments wherein the cross-linkable functional group comprises methacryl). In such embodiments, the second cross-link obtained upon cross-linking is optionally formed by copolymerization of cross-linkable functional groups in the polymer and in the additional cross-linking agent.

In some embodiments of any of the embodiments described herein relating to a polymerizable cross-linkable functional group, the additional cross-linking agent comprises a cross-linkable functional group (as described herein), optionally the same cross-linkable functional groups as in the modified polymer. For example, the additional cross-linking agent may optionally be a monomer corresponding to the cross-linkable functional group (e.g., as described hereinabove); or alternatively, a compound comprising at least two cross-linkable functional groups (e.g., acryl, methacryl, cyanoacryl, or vinylsulfonyl) connected by a linking moiety, for example, a hydrocarbon moiety, or an alkylene glycol (e.g., ethylene glycol or propylene glycol) residue, or dimer, trimer, oligomer or polymer of an alkylene glycol (e.g., a polyethylene glycol moiety), or connected to a nanoparticle or microparticle.

In some embodiments of any of the embodiments described herein relating to a non-polymerizable cross-linkable functional group, the additional cross-linking agent is a compound comprising at least two cross-linkable functional groups (optionally the same cross-linkable functional groups as in the polymer) connected by a linking moiety, for example, a hydrocarbon moiety, or an alkylene glycol (e.g., ethylene glycol or propylene glycol) residue, or dimer, trimer, oligomer or polymer of an alkylene glycol (e.g., a polyethylene glycol moiety), or connected to a nanoparticle or microparticle.

Exemplary Implant Preparation and Delivery

Figure 6A:
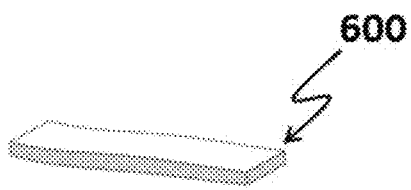
FIG. 6A is an isometric view of an implant compressed, dried and hardened sponge, in accordance with some embodiments of the invention.

In some embodiments, the sponge is optionally made from methacrylic polymer containing methacrylic side groups. Optionally the sponge is made of open porous in different size and shape. In some embodiments, a potential advantage is to have larger size of porous at the center of the sponge than the size of the porous at the edge of the sponge. In some embodiments, the sponge is compressed and optionally stabilized by dehydration, as shown for example in FIG. 6A. In some embodiments, the sponge 600 is optionally immersed in a volatile solution containing initiator for polymerization (e.g. benzoyl peroxide in acetone). In some embodiments, the distribution of the initiator within the sponge is not homogenous. In some embodiments, this enables different polymerization rates in different areas within the sponge. In some embodiments, the immersed sponge 600 is then dried. In some embodiments, the sponge 600 is then slightly absorbed in a solution with no or low solubility to the initiator. In some embodiments, the sponge 600 is then dried and shrinked to a small size optionally using vacuum. The final size and shape of the dry and hardened sponge was optionally shaped to fit to implantation.

Figure 6B:
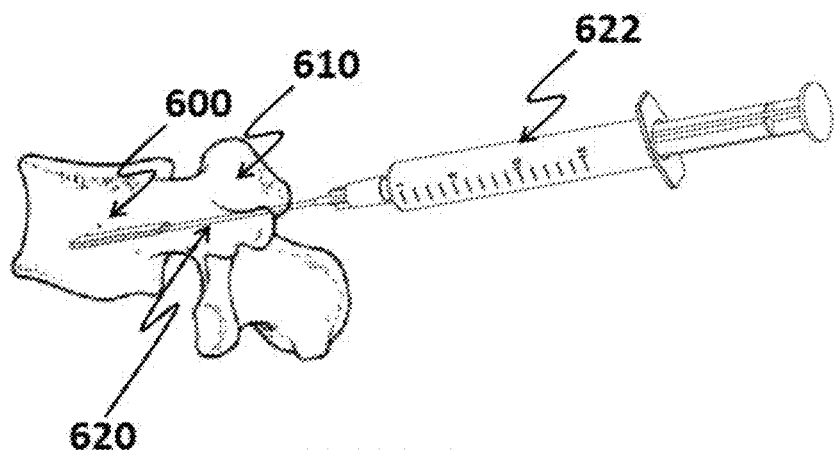
FIG. 6B is an isometric view of the compressed and dried implant sponge placed at the target site, in accordance with some embodiments of the invention.

In some embodiments, the shrinked sponge 600 is implanted, for example in a fractured vertebra 610, as shown, for example in FIG. 6B. In some embodiments, the sponge 600 is attached to needle 620 prior to insertion into the vertebra. In some embodiments, the needle 620 is connected to syringe 622. In some embodiments, the syringe 622 is filled with an acrylic monomers or oligomers solution. Optionally a catalyst is also added to the solution. Optionally the solution contains a softener material that is used to soften the hardened sponge 600. In some embodiments, sponge 600 is connected to needle 620, attached to filled syringe 622, is inserted into fractured vertebra 610, as shown for example in FIG. 6B. In some embodiments, the sponge 600 is inserted into the fractured vertebra 610 prior to connecting to the needle 620. In some embodiments, more than one sponge 600 is inserted to a single fractured vertebra.

Figure 6C:
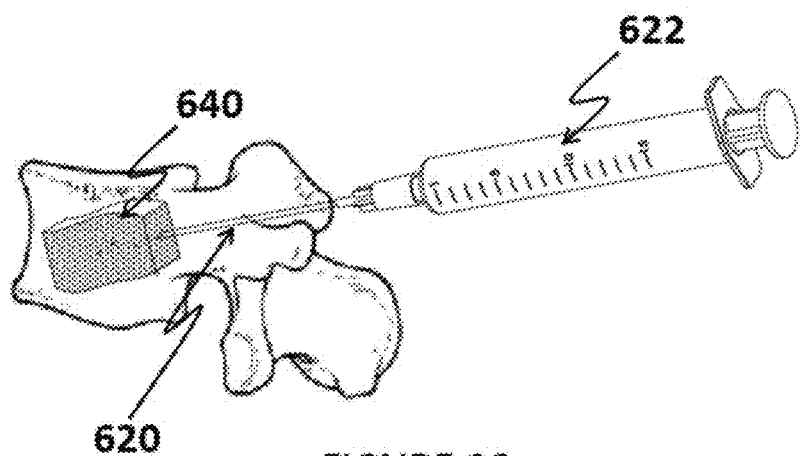
FIG. 6C is an isometric view of the implant sponge during or after expansion, in accordance with some embodiments of the invention.
Figure 6D:
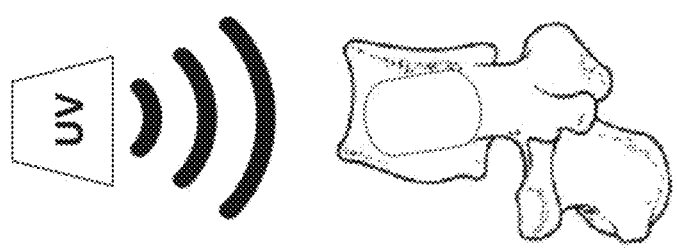
FIG. 6D is an isometric view of the implant curing method by UV radiation, in accordance with some embodiments of the invention.
Figure 6E:
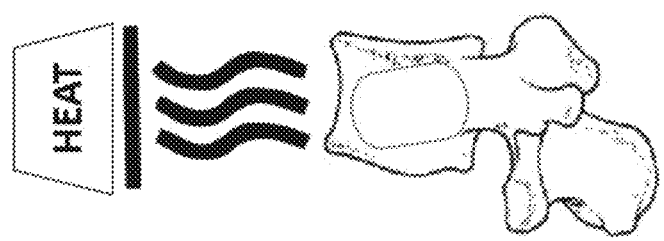
FIG. 6E is an isometric view of the implant curing method by heat radiation, in accordance with some embodiments of the invention.

In some embodiments, a solution is first injected into the sponge 600. In some embodiments, the solution causes the hardened sponge to be softened and expand 640, as shown, for example in FIG. 6C. In some embodiments, during the expansion process the sponge is filled with the acrylic solution injected from the attached syringe 622. In some embodiments, the sponge porous are filled with the solution and a polymerization process occurs between the monomers or oligomers and the acrylic groups of the sponge. In some embodiments, optionally, the polymerization is initiated by the initiator that was prior attached to the sponge. In some embodiments, at the end of the process, a single solid material is made. In some embodiments, the solution filled in syringe 622 is directly injected into the dry and hardened sponge 600. In some embodiments, the sponge 600 is simultaneously softened, filled with the acrylic solution and polymerized. In some embodiments, the syringe 622 and needle 620 are then removed living the implanted sponge 640 in the vertebra. In some embodiments, once the implant is in place and expanded, the curing process is performed by radiating UV to the implant, as shown for example in FIG. 6D. In some embodiments, once the implant is in place and expanded, the curing process is performed by radiating heat to the implant, as shown for example in FIG. 6E.

Exemplary Embodiments of Delivery Device

In some embodiments, the sponge is delivered to the specific location using a dedicated implant delivery device. A side view of one example of an optional design of a delivery device 700, designed to deliver the invented implant, is shown, for example in FIGS. 7A-D. In some embodiments, the delivery device 700 is pre-loaded with the compressed, and optionally dry, implant 702 (see FIG. 7B). In some embodiments, the delivery device 700 comprises an inlet port 704 for filling the delivery device 700 with any kind of liquid (e.g. saline, initiator, uncured cement—720 in FIG. 7C). In some embodiments, the delivery device 700 comprises an outlet port 706 to allow purging and release of excess of liquids or cement after the delivery device is filled. In some embodiments, the delivery device 700 comprises a knob 708 which is used to deliver the implant 702 throughout outlet 710. In some embodiments, the implant 702 is squeezed into delivery tube 712. In some embodiments, a dedicated part 714 is attached to the implant 702 and connected to rod 716. In some embodiments, the other side of rod 716 is connected to piston 718. In some embodiments, the piston 718 can be moved by rotating knob 708. In some embodiments, the rotating knob 708 causes part 714 to advance towards outlet 710. In some embodiments, the part 714 pushes implant 702 out of the delivery tube 712.

Figure 7A:
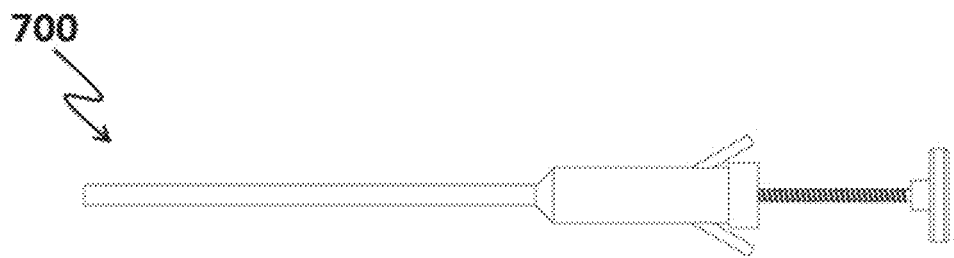
FIG. 7A is a side view of one example of an embodiment of a delivery device, in accordance with some embodiments of the invention.
Figure 7B:
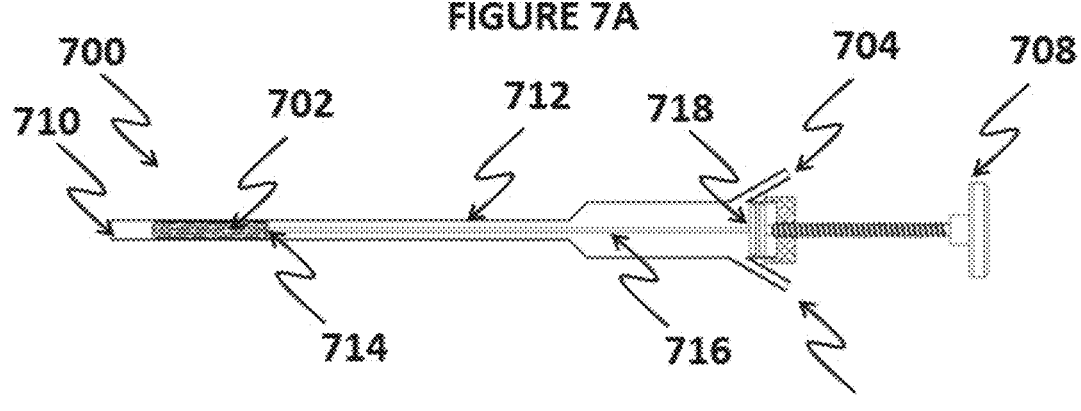
FIG. 7B is a cross section view of one example of an embodiment of the implant delivery device and implant, in the initial configuration, in accordance with some embodiments of the invention.
Figure 7C:
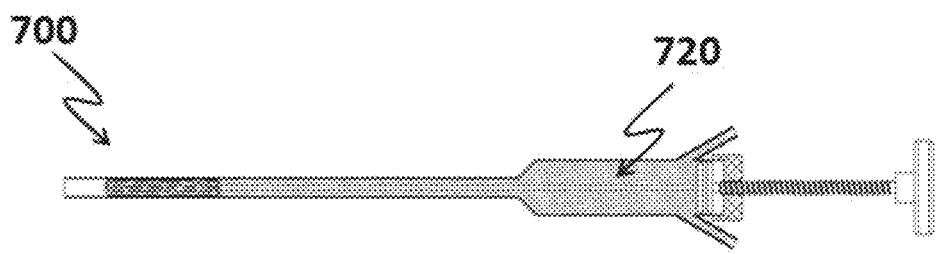
FIG. 7C is a cross section view of one example of an embodiment of the implant delivery device and implant, in the initial configuration, after liquid or uncured cement was filled, in accordance with some embodiments of the invention.
Figure 7D:
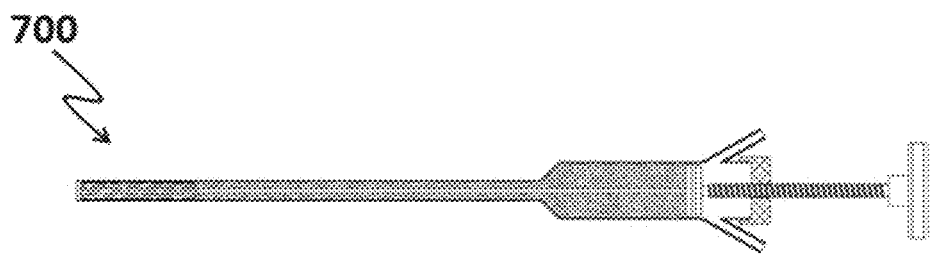
FIG. 7D is a cross section view of one example of an embodiment of the implant and implant delivery device, filled with liquid or uncured cement, where the knob was moved to a ready to deliver configuration, in accordance with some embodiments of the invention.

In some embodiments, in the initial configuration of delivery device, shown for example on FIG. 7B, the piston 718 is positioned before inlet 704 and outlet 706. In some embodiments, in this configuration, the delivery device 700 can be filled with any kind of liquid or uncured cement 720 through inlet port 704. In FIG. 7C it is shown, for example, the delivery device 700 in the configuration described on FIG. 7B, after the liquids or the uncured cement 720 was filled through inlet port 704. In some embodiments, the delivery device 700 is preferably held vertically and the liquids or uncured cement 720 is filled until excessive content reaches outlet port 706. In FIG. 7D it is shown, for example, the delivery device 700, after set-up and in a ready to deliver configuration. In some embodiments, in this configuration, knob 708 was rotated until piston 718 passed inlet 704 and outlet 706. In some embodiments, implant 702 is advanced towards outlet 710. In some embodiments, the implant 702 and liquid or cement 720 are now ready to be delivered.

Figure 7E:
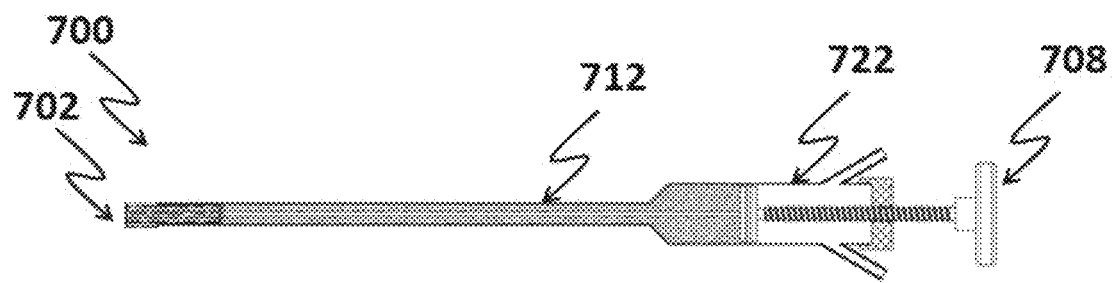
FIG. 7E is a cross section view of one example of an embodiment of the implant delivery device and implant during implant delivery configuration, where the implant is partly delivered, in accordance with some embodiments of the invention.

In FIG. 7E it is shown, for example, the delivery device 700 during the implant 702 delivery. In some embodiments, this procedure is done after the delivery device 700 was positioned in the delivery target site. In some embodiments, optionally the delivery procedure is a minimally invasive procedure. In some embodiments, knob 708 is rotated and pushes the piston 718 that pushes the liquid or uncured cement 720 enabling the implant 702 to absorb the liquids or cement while exiting the delivery device 700 and swelling. In some embodiments, the extruded part of the implant 702 volume increases because of liquid of cement absorption and/or elastic properties. In some embodiments, in this configuration only part of the implant 702 is delivered. In some embodiments, the delivery device 700 is optionally designed in differences between the piston syringe 722 and the delivery tube 712 cross-section areas. In some embodiments, this is done to deliver larger or smaller volume of liquid or uncured cement 720 compared to the volume of the implant 702 that is released. In some embodiments, this enables the supply of required volume of liquid or uncured cement that is absorbed by the implant throughout the procedure.

Figure 7F:
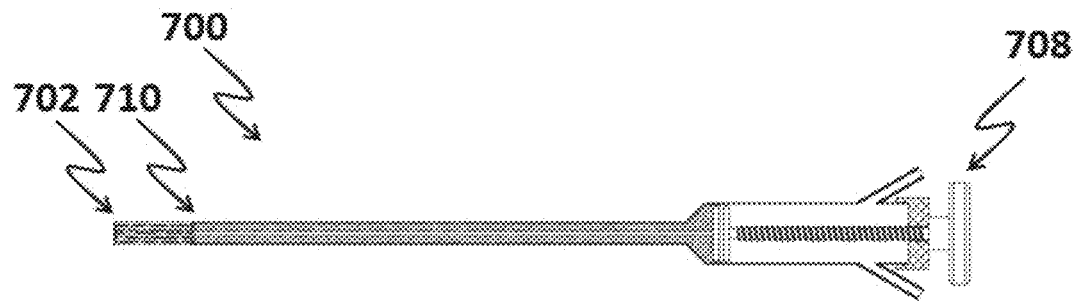
FIG. 7F is a cross section view of one example of an embodiment of the implant delivery device and implant, and the implant is fully delivered, in accordance with some embodiments of the invention.
Figure 7G:
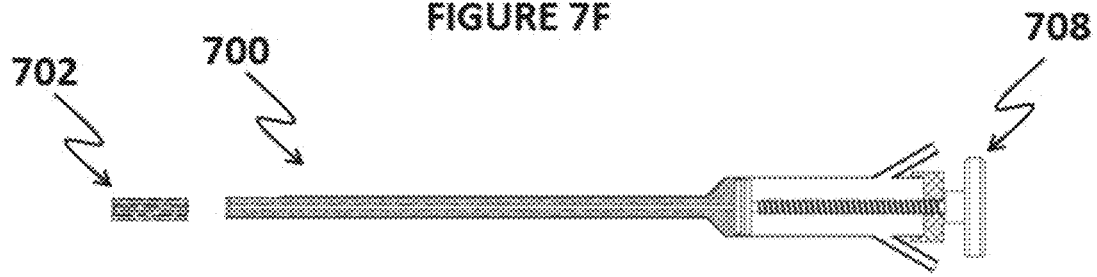
FIG. 7G is a cross section view of one example of an embodiment of the implant delivery device and implant, the implant is fully delivered and the delivery device is extracted, in accordance with some embodiments of the invention.

In FIG. 7F it is shown, for example, the delivery device 700 after knob 708 was fully rotated. In some embodiments, in this configuration implant 702 is completely released throughout port 710.

In FIG. 7F it is shown, for example, the delivery device 700 after implant 702 was delivered and delivery device 700 is detached from implant 702. In some embodiments, the delivery device 700 is removed and the implant 702 is left in the target site. In some embodiments, the liquids or uncured cement, cure the implant, forming a solid implant.

Figure 8:
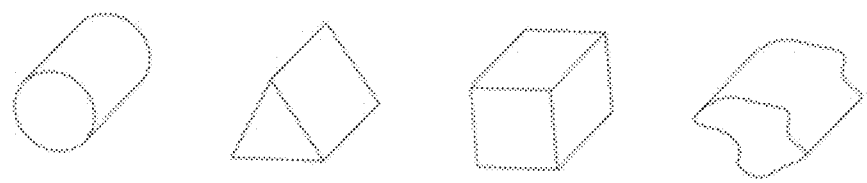
FIG. 8 is an illustration view of some of optional size and shapes of the implant, before or after execution, in accordance with some embodiments of the invention.

In FIG. 8 it is shown, for example, an illustrative view of some optional shapes of the implants 702. In some embodiments, implant 702 can be implemented in any required size and shape before and after implant.

In some embodiments, the quantity of liquids or cement, required for the complete curing of the implant is from about 0.5 ml to about 10 ml.

In some embodiments, the quantity of liquids or cement, required for the complete curing of the implant is from about 1% to about 10% of the total weight of the implant. In some embodiments, the quantity of liquids or cement, required for the complete curing of the implant is from about 100% to about 300% of the total weight of the implant.

In some embodiments, the quantity of liquids or cement used for the complete curing of the implant is modified according to: the void volume of implantation site and/or the final desired density of the implant and/or the final required stiffness and/or the desired rate of curing and/or the application.

In some embodiments, the time for the curing process with liquid is from about 2 minutes to about 30 minutes for 80% of curing. In some embodiments, the time for the curing process with liquid is from about 5 minutes to about 20 minutes for 80% of curing. In some embodiments, the time for the curing process with liquid is from about 7 minutes to about 10 minutes for 80% of curing.

In some embodiments, the time for the curing process with liquid is from about 1 hour to about 8 hours for 100% of curing. In some embodiments, the time for the curing process with liquid is from about 2 hour to about 6 hours for 100% of curing. In some embodiments, the time for the curing process with liquid is from about 3 hour to about 4 hours for 100% of curing.

In some embodiments, the curing of the delivered implant is performed by exposing the implant to ultraviolet (UV) radiation. Adding photoinitiator (e.g. dimethoxy-diphenyl-ethan-one or benzophenone) to the sponge and radiating it with UV light (254-350 nm), will produces free radicals in the sponge. The radicals would start a chain reaction between the methacrylic groups to form crosslinking network. The radiation of the implant can be achieved by inserting optic fiber to the implantation site.

In some embodiments, the time for the curing process with UV is from about 2 seconds to about 3 minutes for 80% of curing. In some embodiments, the time for the curing process with UV is from about 10 seconds to about 2 minutes for 80% of curing. In some embodiments, the time for the curing process with UV is from about 30 seconds to about 1 minutes for 80% of curing.

In some embodiments, the time for the curing process with UV is from about 1 hour to about 8 hours for 100% of curing. In some embodiments, the time for the curing process with UV is from about 2 hour to about 6 hours for 100% of curing. In some embodiments, the time for the curing process with UV is from about 3 hour to about 4 hours for 100% of curing.

In some embodiments, the curing of the delivered implant is performed by exposing the implant to specific temperatures. In some embodiments, a thermal initiator (e.g. Azobis [2-(2-imidazolin-2-yl)propane]dihydrochloride) is added to the sponge and then, the implant is heated at a temperature from about 40 degrees Celsius to about 60 degrees Celsius. In some embodiments, the temperature of the heating is from about 45 degrees Celsius to about 55 degrees Celsius. The heating will produce free radicals in the sponge. The radicals would start a chain reaction between the methacrylic groups to form crosslinking network. The heating of the implant can be achieved by inserting heating probe to the implantation site.

In some embodiments, the time for the curing process with heat is from about 2 minutes to about 30 minutes for 80% of curing. In some embodiments, the time for the curing process with heat is from about 5 minutes to about 20 minutes for 80% of curing. In some embodiments, the time for the curing process with heat is from about 7 minutes to about 10 minutes for 80% of curing.

In some embodiments, the time for the curing process with heat is from about 1 hour to about 8 hours for 100% of curing. In some embodiments, the time for the curing process with heat is from about 2 hour to about 6 hours for 100% of curing. In some embodiments, the time for the curing process with heat is from about 3 hour to about 4 hours for 100% of curing.

Exemplary Mechanical Characteristics

In some embodiments, the implant in its soft configuration comprises the following characteristics:

Directionality

In some embodiments, the implant comprises in order to introduce directionally to the implant. The sponge can be produce by layers instead of as one bulk. In this case after crosslinking and hardening of the sponge it will receive different elasticity in different directions Porosity In some embodiments, porosity or void fraction is a measure of the void (i.e. "empty") spaces in the material, and is a fraction of the volume of voids over the total volume, between 0 and 1, or as a percentage between 0% and 100%.

In some embodiments, the porosity percentage (%): from about 60% to about 100%. In some embodiments, the porosity percentage is from about 70% to about 90%. In some embodiments, the porosity percentage is from about 75% to about 85%. In some embodiments, different porosity is achieved by controlling the density of the cross-linker at different regions of the implant and by using different wetting agents in the foaming stage of the implant production. In some embodiments, the implant is produced by layers instead of one bulk. This will enable non-homogenous distribution of the porous in the sponge, that is, different concentration and porous sizes at different sites.

Pore Size

In some embodiments, the pore size (um): is from about 50 um to about 3000 um. In some embodiments, the pore size (um): is from about 100 um to about 2000 um. In some embodiments, the pore size (um): is from about 500 μm to about 1000 um.

Density

In some embodiments, the density ($g/cm^3$): is from about 0.05 $g/cm^3$ to about 0.5 $g/cm^3$. In some embodiments, the density ($g/cm^3$): is from about 0.1 $g/cm^3$ to about 0.4 $g/cm^3$. In some embodiments, the density ($g/cm^3$): is from about 0.1 $g/cm^3$ to about 0.2 $g/cm^3$.

Elastic Modulus

In some embodiments, the elastic modulus (MPa): is from about 0.001 MPa to about 1 MPa. In some embodiments, the elastic modulus (MPa): is from about 0.01 MPa to about 0.1 MPa. In some embodiments, the elastic modulus (MPa): is from about 0.05 MPa to about 0.1 MPa. In some embodiments, the elastic modulus is selected according to the specific site to which will be implanted. In some embodiments, different elasticity is achieved by controlling the density of the cross-linker at different regions of the implant. In some embodiments, at high density, the implant is characterized by a higher modulus of elasticity and vice versa. In some embodiments, the implant is produced by layers instead of one bulk. This will enable controlling the direction of elasticity so that the final hardened implant will have higher elasticity in one direction and lower in another.

In some embodiments, the implant in its hard (or stiff) configuration comprises the following characteristics:

Porosity

In some embodiments, the porosity percentage (%): from about 60% to about 100%. In some embodiments, the porosity percentage is from about 70% to about 90%. In some embodiments, the porosity percentage is from about 75% to about 85%.

Pore Size

In some embodiments, the pore size (um): is from about 50 um to about 3000 um. In some embodiments, the pore size (um): is from about 100 um to about 2000 um. In some embodiments, the pore size (um): is from about 500 um to about 1000 um.

Density

In some embodiments, the density ($g/cm^2$): is from about 0.05 $g/cm^2$ to about 0.5 $g/cm^2$. In some embodiments, the density ($g/cm^2$): is from about 0.1 $g/cm^2$ to about 0.4 $g/cm^2$. In some embodiments, the density ($g/cm^2$): is from about 0.1 $g/cm^2$ to about 0.2 $g/cm^2$.

Elastic Modulus

In some embodiments, the elastic modulus (MPa): is from about 1 MPa to about 500 MPa. In some embodiments, the elastic modulus (MPa): is from about 2 MPa to about 150 MPa. In some embodiments, the elastic modulus (MPa): is from about 5 MPa to about 100 MPa.

Exemplary Procedures

Figure 9A:
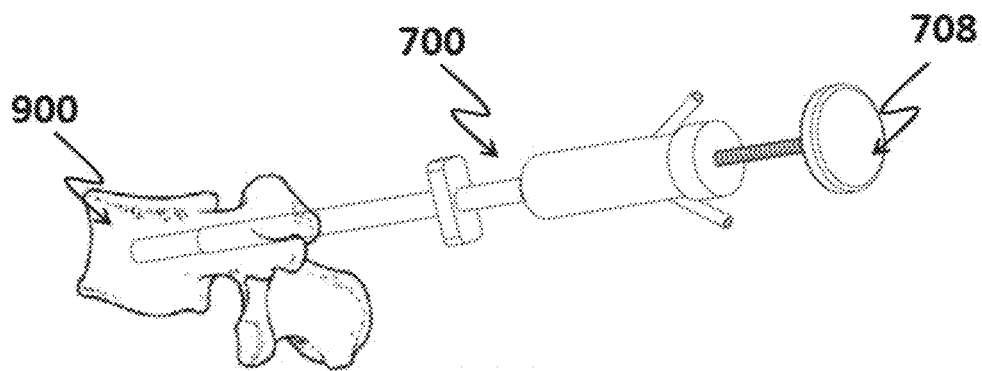
FIG. 9A is an isometric view of one example of an embodiment of the delivery device during a Vertebroplasty or Kyphoplasty procedure, and the delivery device is positioned in the vertebrae target site, in accordance with some embodiments of the invention.
Figure 9B:
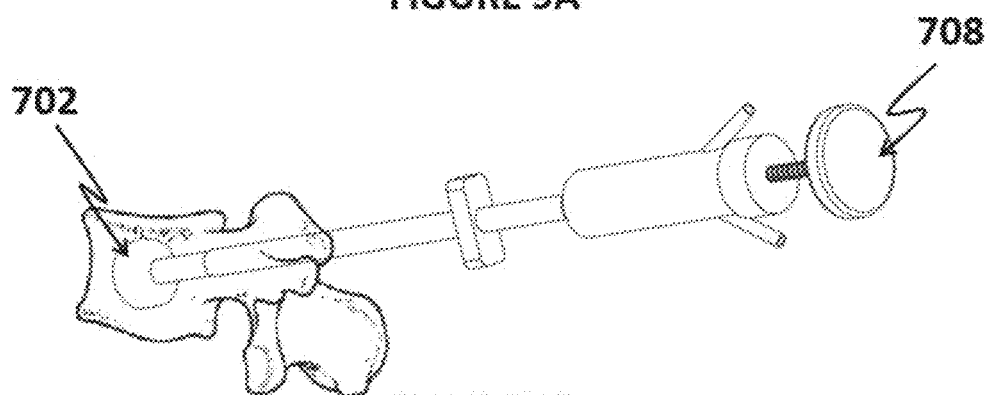
FIG. 9B is an isometric view of one example of an embodiment of the delivery device during a Vertebroplasty or Kyphoplasty procedure and the implant is partly delivered, in accordance with some embodiments of the invention.
Figure 9C:
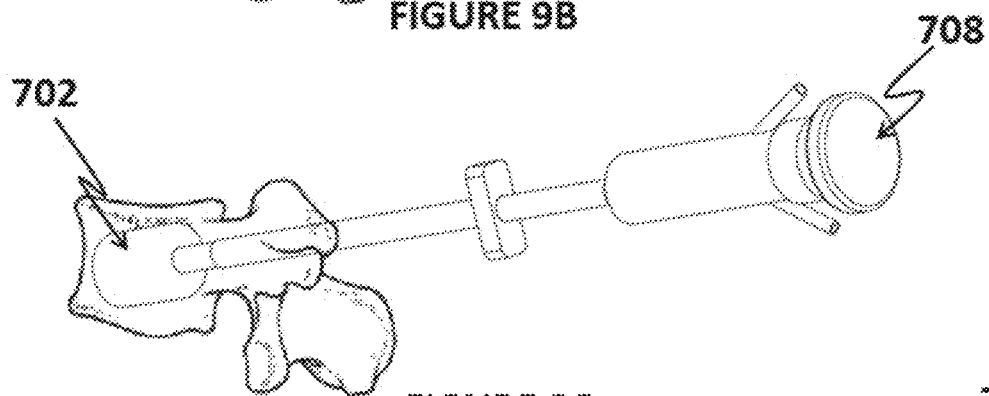
FIG. 9C is an isometric view of one example of an embodiment of the delivery device during a Vertebroplasty or Kyphoplasty procedure and the implant is fully delivered, in accordance with some embodiments of the invention.
Figure 9D:
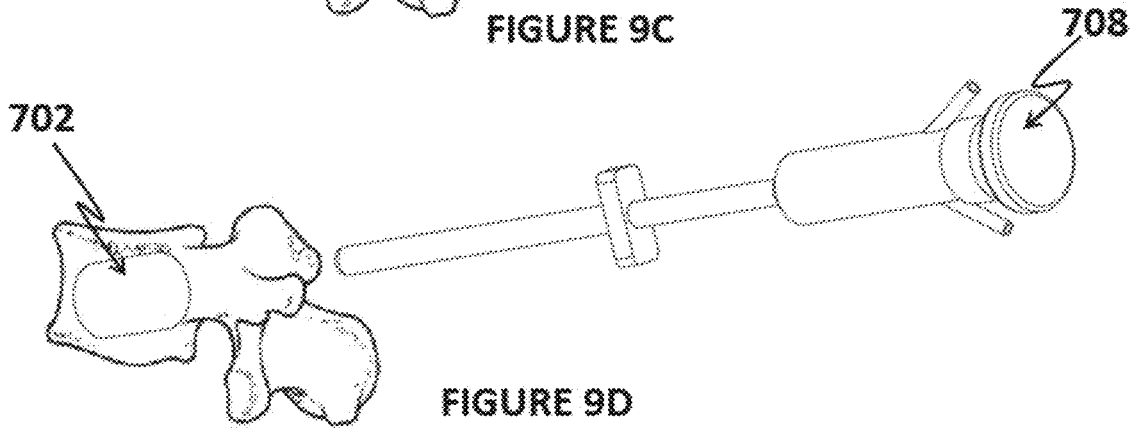
FIG. 9D is an isometric view of one example of an embodiment of the delivery device during a Vertebroplasty or Kyphoplasty procedure and the implant is fully delivered and the delivery device is extracted, in accordance with some embodiments of the invention.

FIGS. 9A to 9D are an illustrative view of a procedure according to some embodiments, applied with this invention. In these figures, a Vertebroplasty or Kyphoplasy procedure is shown. On FIG. 9A a fractured vertebra 900 is shown. In some embodiments, the delivery device 700 is inserted, optionally in a trans-pedicular procedure through cannula 902. In some embodiments, the implant is optionally introduced after creating a void using a Kyphoplasty balloon, or with no prior void creation, during Vertebroplasty procedure. In this figure, the delivery device 700 and implant 702 are in the configuration described on FIG. 7D. In some embodiments, the delivery device is introduced to the target site. FIG. 9B shows the delivery device 700 and implant 702 in the configuration described on FIG. 7E, after knob 708 was partly rotated and part of the implant 702 is delivered and expanded. FIG. 9C shows the delivery device 700 and implant 702 in the configuration described on FIG. 7F, after knob 708 was fully rotated and implant 702 is completely delivered. FIG. 9D is an illustrative view of the delivery device 700 and cannula 902, after removal from the treated vertebra via completion of implant 702 delivery, according to some embodiments. In some embodiments, the implant 702 is placed in the target site at the fractured vertebrae. In some embodiments, the implant 702 is expanded to its final shape or in the shape determined by the vertebrae anatomy. In some embodiments, the uncured implant is cured to a solid structure.

Figure 10A:
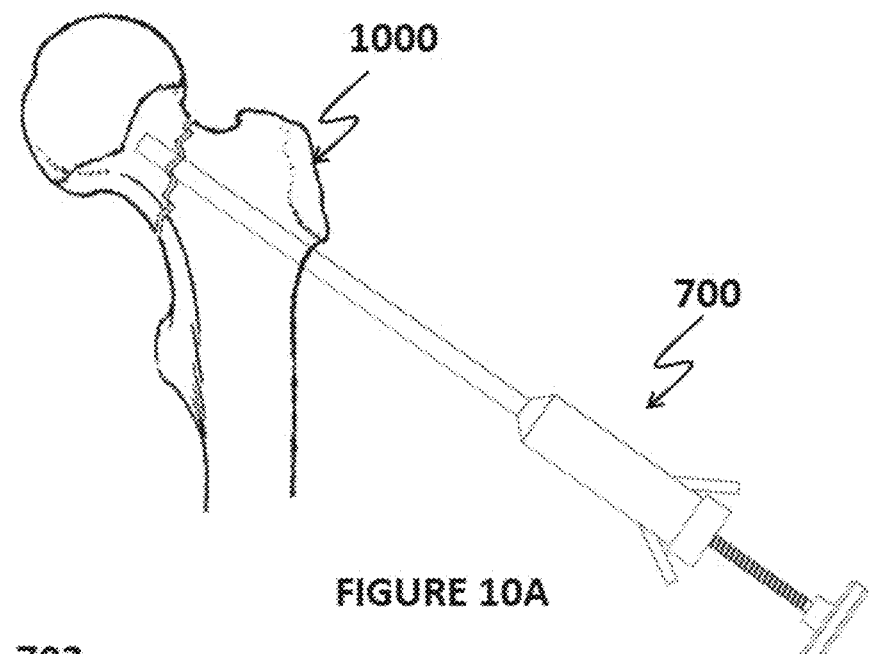
FIG. 10A is a side view of one example of an embodiment of the delivery device during femoral neck fracture procedure and the delivery device is positioned at the implant placement site, in accordance with some embodiments of the invention.
Figure 10B:
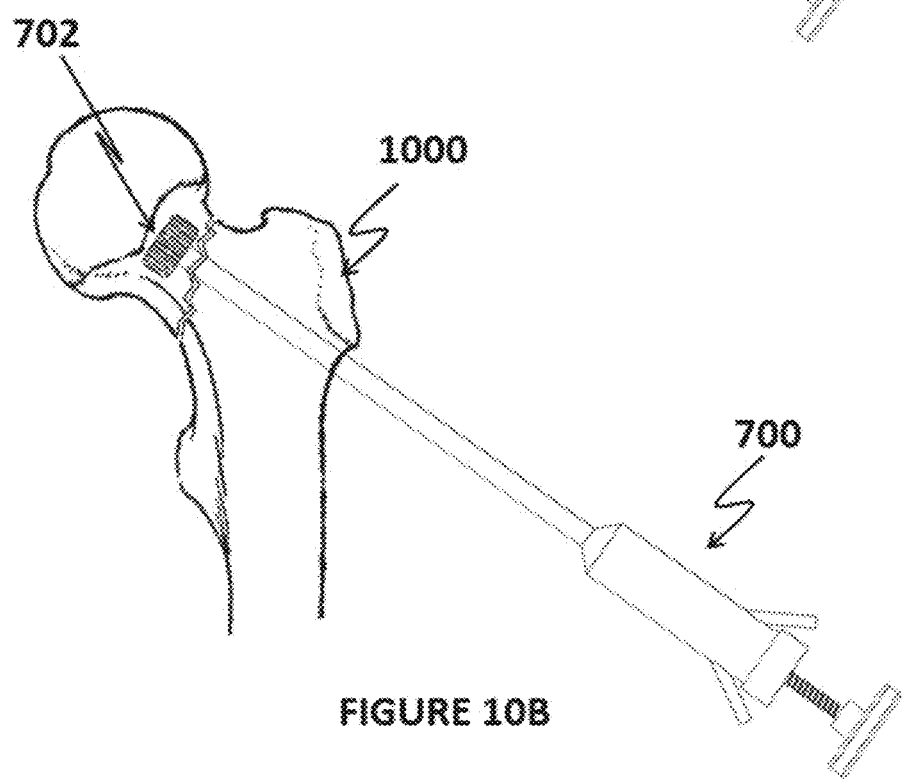
FIG. 10B is a side view of one example of an embodiment of the delivery device during femoral neck fracture procedure and the implant is partly delivered, in accordance with some embodiments of the invention.
Figure 10C:
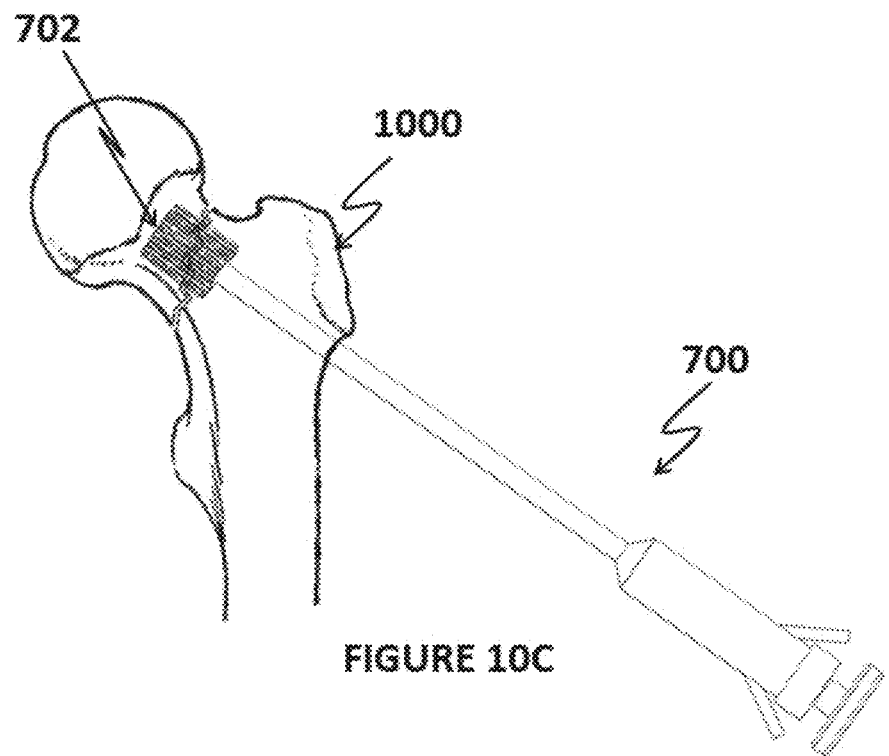
FIG. 10C is a side view of one example of an embodiment of the delivery device during femoral neck fracture procedure and the implant is fully delivered, in accordance with some embodiments of the invention.
Figure 10D:
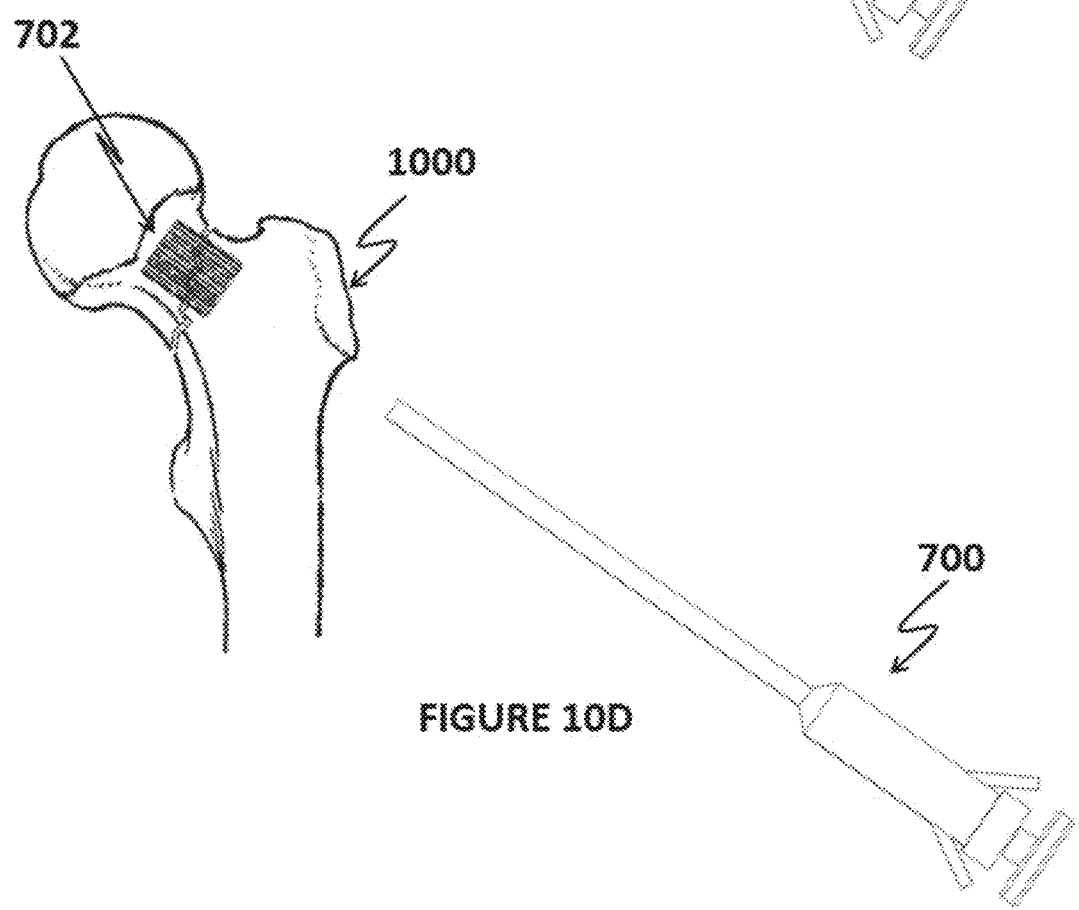
FIG. 10D is a side view of one example of an embodiment of the delivery device during femoral neck fracture procedure and the implant is fully delivered and the delivery device is extracted, in accordance with some embodiments of the invention.

FIGS. 10A to 10D are an illustrative view of one alternative procedure applied with some embodiments of this invention. In these figures, a fixation of non-displaced or impacted femoral neck fractures is shown. In some embodiments, this procedure is optionally done percutaneously. In some embodiments, the delivery device 700 in configuration described on FIG. 7D is inserted to a fractured femoral 1000 in a direct lateral approach, optionally through a cannula (not shown). In some embodiments, the delivery device outlet 710 is optionally positioned distal to fracture 1002. FIG. 10B shows the delivery device 700 and implant 702 after knob 708 was rotated and implant 702 was partially delivered. FIG. 10C shows the delivery device 700 and implant 702 after knob 708 was fully rotated and implant 702 is placed in the target site. In some embodiments, the implant 702 is positioned in-between the fracture 1002 portions to generate robust fixture. FIG. 10D shows the delivery device 700 after removal from the fractured femoral 1000. In some embodiments, the implant 702 is expanded to its final shape or in the shape determined by the vertebrae anatomy. In some embodiments, the implant is cured to a solid structure. Optionally, additional support and rotational stability is done by screws placement before or after this procedure.

Figure 11A:
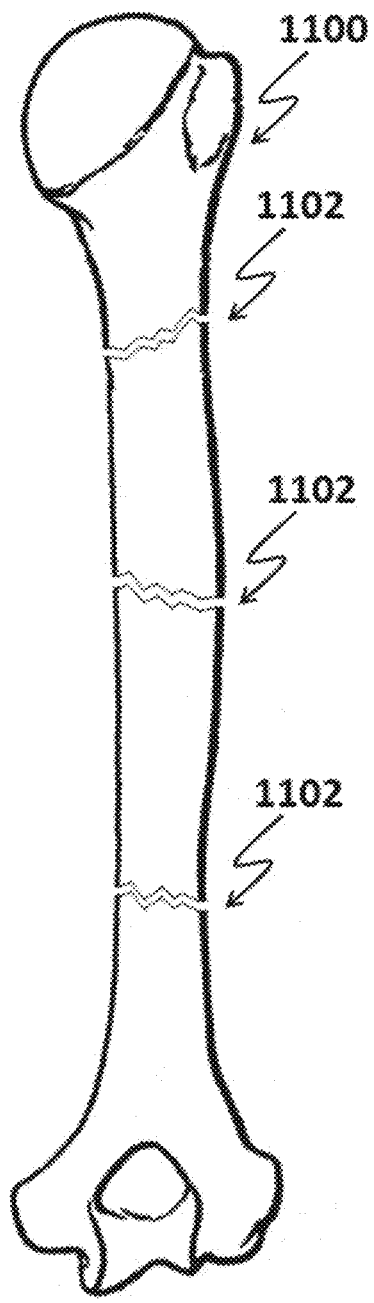
FIG. 11A is a side view of a bone having more than one fracture, in accordance with some embodiments of the invention.
Figure 11B:
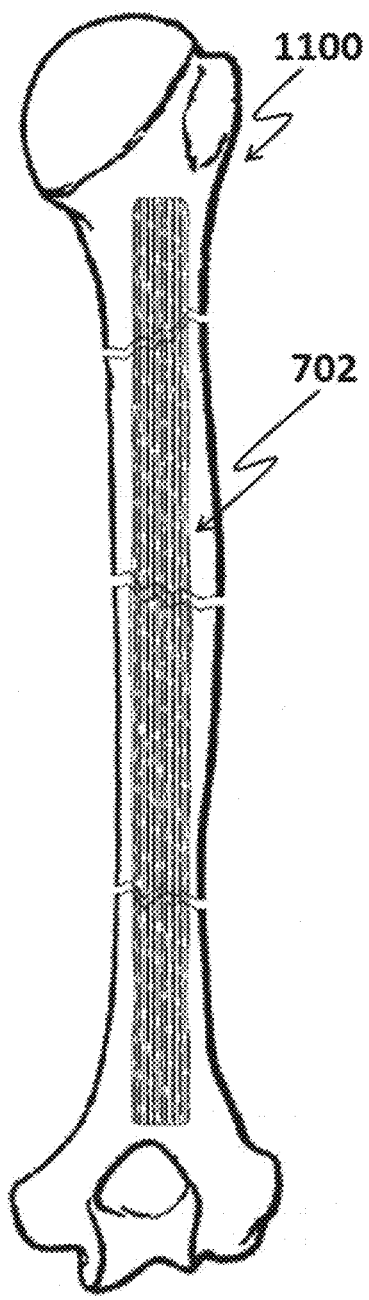
FIG. 11B is a side view of the bone shown on FIG. 11A, after a long implant was placed to treat more than one fracture, in accordance with some embodiments of the invention.

FIG. 11A is a side view of a bone 1100 having numerous fractures 1102. In some embodiments, these types of fractures are treated with implanted nails and or plates and screws. FIG. 11B schematically shows the use of the implant 702 to treat a bone having multiple fractures. In some embodiments, the implant 702 is positioned inside the fractured bone 1100. Optionally, additional implants e.g. plates and screws are used.

Figure 12:
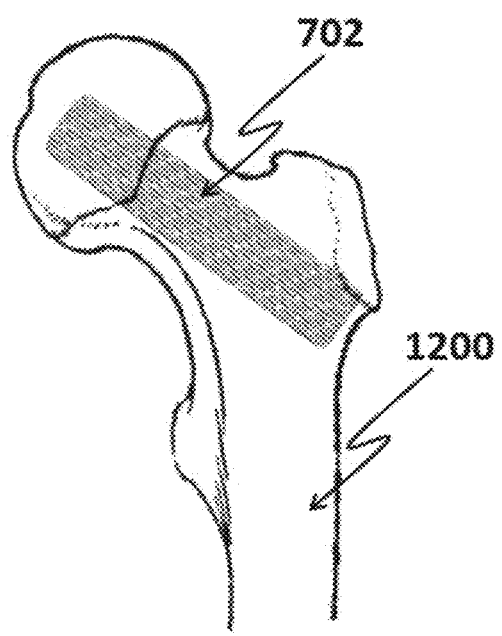
FIG. 12 is a side view of an osteoporotic bone with no fracture. The implant was placed to strengthen the bone and reduce the risk for fracture, in accordance with some embodiments of the invention.

FIG. 12 shows a bone 1200 that is not fractured or having only micro fractures. In this case the bone 1200 is in a risk of fracture because of osteoporotic or other causes. In some embodiments, in order to prevent or reduce the risks for future fraction, the implant 702 is implanted and thereby strengthens the bone and reduces the risk for future fracture.

General Exemplary Medical Applications

In some embodiments, the biocompatible soft sponge implant, having the ability to harden following initiation, is used in various applications in the medical field. In some embodiments, each of the following applications comprises a potential advantage over state of the art solutions.

Below are several examples within the medical field, where the implant can be used. The examples below are provided for a human body, but it is clear that any of the following can be implemented on animals too.

Treating Fractured Bones

The human skeleton is composed of 270 bones at birth. Any of these bones may suffer a fracture during its lifetime. Fractures may be caused due to traumatic incidents or due to medical conditions that weaken the bone, such as osteoporosis or bone cancer. In some cases, it is the combination of a weak bone and a minor trauma that causes a fracture.

In order to reduce pain and restore fractured bone shape, in cases of dislocation, a reduction and stabilization procedure is done. Different techniques are used to stabilize a fractured bone, depends on the bone location, the fracture severity and the procedure chose. In some cases, an external fixation like plaster cast or braces are used. In some cases, metal rods or plates are used to hold the bone pieces together.

In some embodiments, the implant is used as an alternative or in addition to current solutions. In some embodiments, the implant is inserted into a fractured bone, optionally, in a minimally invasive percutaneous procedure. In some embodiments, the implant is inserted as a solid and soft material. In some embodiments, once the implant is placed at the target site, an initiation process is triggered. In some embodiments, the implant is hardened and holds the bone fractured pieces in a restored position. In some embodiments, this solution has the potential for better treatment with less surgical trauma, especially in fractures where access is more limited. In some embodiments, some examples are; hip fracture, rib fracture and clavicle fracture.

Strengthening a Weak Bone in Order to Prevent Fracture

Worldwide osteoporosis causes more than 9 million fractures annually. Of which 1.6 million hip fractures, 1.7 million forearm and 1.4 million are vertebral fractures. Bone metastases also cause bone loss and increase the risk for bone fracture.

In some cases, a surgical prevention procedure is done with the aim of increasing the resistance of a weak bone e.g. femoral neck to the compression and distraction forces acting on it, though reduce the risk for fracture. The first surgical reinforcement of the femoral neck was proposed for the first time in 1960. Stainless-steel nails where inserted in a percutaneous procedure, under local anesthesia. A more recently approach is called "femoroplasty" consisting of injection of poly-methyl-methacrylate (PMMA) inside osteoporotic femoral neck. However, one of the big concerns in the application of this technique is the high volume of PMMA necessary which generates enormous heat during polymerization, leading to necrosis of the femoral head.

In some embodiments, the implant is used for this application, instead of the current used PMMA, thus eliminating the heat generated. In some embodiments, the implant is used together with the PMMA, thus reducing the amount of PMMA needed and therefor reducing the heat generated. In some embodiments, the implant has osteoconductive properties which allow bone growth at the implantation site.

Bone Substitute and Augmentation

Over two million bone grafting procedures are performed worldwide per year. The use of autografts, harvested from the patient's own body as bone substitution is in most cases preferred but morbidity and limited availability are the main limitations. Allografts, obtained from a bone bank still raise concerns about the residual infective risks, costs and donor availability issues.

As an alternative, several bone substitutes were developed; Xenograft bone substitutes have their origin from a species other than human. Bovine bone is usually used. Some type of corals maybe harvested and treated to become coral based xenografts.

Ceramics bone substitutes are calcium based substitutes made of Hydroxyapatite and TCP (Tricalcium Phosphate).

Calcium phosphate cements (CPC) are synthetic bone substitutes. A white powder, consisting of calcium phosphate, that when mixed with a liquid, forms a workable paste which can be shaped during surgery to fit the contours of bone loss. The cements hardening reaction, which forms nanocrystalline hydroxyapatite (HA) is isothermic and occurs at physiologic pH so tissue damage does not occur during the setting reaction.

Polymer-based bone graft substitutes have physical, mechanical, and chemical properties completely different from the other bone substitutes. The polymers can be divided into natural polymers and synthetic polymers. Polymers such as PMMA and various other acrylates are used for their mechanical resilience and biocompatibility.

In some embodiments, the implant is used as bone substitute for filling small gaps as well as large voids. In some embodiments, in addition to the mechanical strengthening and bone stabilizing, the implant may serve as an osteoconductive scaffold material enabling new bone growth. In some embodiments, the implant is applied on any bone in the body including bone augmentations for dental applications.

Anchoring Applications

Many surgical procedures require adequate attachment of soft tissues such as tendons and ligaments to a bone. This has been one of the most difficult aspects in orthopedic surgery. For this to occur in a natural soft tissue healing, the tissue needs to be maintained in a position of contact by immobilizing the limb for a long period of time.

In order to improve the fixation strength and placement, several techniques were developed. Techniques involve the drilling of bone tunnels, with or without pull through sutures, or may use fixation of soft tissues to bone using screws and washers.

Bone fasteners and toggle anchors are sometimes used and require a larger access to the underlying bone with a higher potential for damage during the implant insertion. Over the last decade, more advanced technologies were developed; current designs of bone anchors allow them to be inserted arthroscopically or through a very small per-cutaneous incision. Bio-absorbable anchors were developed, having equal pullout strength to the metal anchors. Biodegradable polymers were developed and are currently found in modern anchors include poly-L-lactic acid, poly-D, L lactic acid, polydioxanone, polyglycolic acid and their copolymers. Acrylic bone cements are also widely used in orthopaedic applications to anchor implants to existing bone.

The main complications experienced with anchor devices are; migration or breakage of the device, infections and limitations in anchor placement and removal.

Few examples where anchoring is requires are; Avulsion fractures, Bicipital Tendon Injuries, Collateral Ligament Pathology (Knee), Distal Humerus Fractures, Knee Dislocations, Lateral Epicondylitis, Mannerfelt Syndrome, Meniscal repair, Medial Humeral Condyle Fracture, Patellar Tendon Rupture, Perilunate Fracture Dislocations, Posterior Glenohumeral Instability, Quadriceps Tendon Rupture, Recurrent Ankle Sprains, Stener Lesion, Superior Labral Lesions, Superior Labrum Lesions, Triangular Fibrocartilage Complex Injuries and Wrist Arthroscopy.

In some embodiments, the implant is used as an anchoring material, connecting a bone to a soft tissue. In some embodiments, the implant is used as a standalone implant or as an additive to existing solutions.

Artificial Cartilage and Disc Implant

Articular cartilage is a connective tissue of diarthrodial joints. Its principal function is to provide a smooth, lubricated surface for articulation and to facilitate the transmission of loads with a low frictional coefficient. Cartilage has limited repair capabilities because chondrocytes are bound in lacunae and cannot migrate to damaged areas. Injury or diseases like; Osteoarthritis, Achondroplasia, Costochondritis, Spinal disc herniation, Relapsing polychondritis and Relapsing polychondritis can affect and damage the cartilage.

Biomaterials currently used for cartilage replacement/regeneration are; Hydrogels like Poly vinyl alcohol (PVA), Polyacrylates, Poly (N-isopropylacrylamide) and Amidated polysaccharide hydrogel. Other materials used are silicon rubber and polymeric composite materials.

The quest for an ideal material that could mimic and replace damaged articular cartilage tissue, has been the focus of several past and current researches. Metals, ceramics and ultrahigh molecular weight polyethylene (UHMWPE) have shown some success. However, there is still a need to develop materials that would possess frictionless lubrication, Provide sufficient cushion effect against shocks, have excellent wear resistant, will be biocompatible and will have simple and firm attachment mechanism to the underlying bone.

In some embodiments, the implant overcomes some of the current limitation of materials used today. In some embodiments, the implant is applied in a form of sponge like or in a form of a dense material for the use as artificial cartilage or disc. In some embodiments, the implant used for artificial cartilage or disc applications, is placed at the target site, having certain material properties enabling efficient delivery to the target site. Then an initiation process changes its material properties to fit to the artificial implant requirements.

Arthrodesis (Joint Fusion)

When a damaged joint cannot be managed by pain medication, splints, or other normally indicated treatments, an arthrodesis surgery, also known as artificial ankylosis may be done. In this fusion surgery, a bone graft and/or instruments are used to encourage bone growth over the joint and create one immobile unit. Joint fusion can effectively reduce pain. This procedure is most commonly performed on joints in the spine, hand, ankle, and foot.

In order to facilitate bony fusion, a bone graft can be placed between the two bones using a bone from elsewhere in the person's body (autograft) or using donor bone (allograft) from a bone bank. In some cases, a variety of synthetic bone substitutes are used. These are usually hydroxyapatite- or tricalcium phosphate-based granules formed into a coralline or trabecular structure to mimic the structure of cancellous bone. The bone graft act solely as an osteoconductive matrix. In other cases, metal implants can be attached to the two bones to hold them together in a position which favors bone growth. Sometimes a combination of the above methods is also employed.

In some embodiments, the implant is used in these procedures. In some embodiments, the implant is placed between two bones, with or without a bone graft, and form an osteoconductive matrix enabling bone growth and fusion. In some embodiments, the implant may also act as a mechanical fixation together with solid implants or as a standalone implant to eliminate movement and hold the joint in a preferred position.

Cosmetic Implants

Cosmetic implants are used in dentistry, breast augmentation surgeries and face reconstructive surgeries. Cosmetic implants are also used to enhance the shape of buttocks, calf, and pectoral regions. Implants are made of Polymers, Metals, Ceramics, and Biomaterials. Tumor removal, laceration repair, maxillofacial surgery, scar revision and hand surgery are the common reconstruction procedures done by cosmetic implants.

In some embodiments, the implant is used as an implant for cosmetic applications. In some embodiments, the implant comprises a pre-formed final size and shape or can be shaped by a surgeon at the time and place of surgery. In some embodiments, the implant is placed under an open surgery or in a minimally invasive procedure, through a small incision. Optionally, the implant is inserted while having material properties enabling the delivery through a small size tube and only after placed at target site, a triggering mechanism changes the implant properties to fit best for the application. In some embodiments, the implant acts as osteoconductive matrix for cosmetic surgeries were bone additive is needed. In some embodiments, the implant is in a softer form and serve as a growth substrate for soft tissue.

General Exemplary Non-Medical Applications

In some embodiments, the materials used as medical grade implants are used in non-medical applications. In some embodiments, the materials are non-medical graded materials. The methods described before apply also here.

Some non-limiting examples of non-medical use are: void filling for construction or aviation (where a lightweight material is needed), gluing substitutes anchoring (screw anchor), art, crafting, prototypes fabrication, temperature isolation (since it is porous), and fluids filtration.

Examples of Manufacture

Materials:

1,3-Butadiene diepoxide (>97%) was obtained from Aldrich.

Decane (>95%) was obtained from Aldrich.

Dibutyltin dilaurate (DBTDL) (>99%) was obtained from Sigma-Aldrich.

DMSO (>99.7%) was obtained from Sigma-Aldrich.

2-Isocyantoethyl methacrylate (>98%) was obtained from Aldrich.

Glycidyl methacrylate (>97%) was obtained from Aldrich.

Hexamethylene diisocyanate (>98%) was obtained from Sigma-Aldrich.

Hydrochloric acid (37%) was obtained from Sigma-Aldrich.

Methacrylic anhydride (94%) was obtained from Aldrich.

Paraformaldehyde (or any formaldehyde releasing molecule such as paraformaldehyde) was obtained from Sigma-Aldrich.

Pluronic™ P123 was obtained from Sigma-Aldrich.

Poly(vinyl alcohol) (Mowiol™ 20-98, 125 kg/mol) was obtained from Sigma-Aldrich.

Silicone oil was obtained from Fisher.

Sulfuric acid (98%) was obtained from Sigma-Aldrich.

Triethylamine (>99%) was obtained from Sigma-Aldrich.

Triton™ X-405 surfactant (70%) was obtained from Sigma-Aldrich.

Preparation of Curable Sponges

General Procedure:

Preparation of exemplary curable sponges comprises by two processes: a) attachment of cross-linkable functional groups (e.g., methacrylate) to a polymer (e.g., poly(vinyl alcohol)) to obtain a cross-linkable modified polymer; and b) preparation of a sponge from the polymer (or modified polymer) by further crosslinking with a cross-linker (e.g., formaldehyde) to obtain a cross-linked polymer comprising a first cross-link, wherein cross-linking is optionally effected in the presence of gas bubbles in order to obtain a sponge structure. The two processes may optionally be performed sequentially, in any order, or in a concomitantly.

Using the above general procedure, various exemplary sponges were prepared according to the procedures described below.

A. Poly(Vinyl Alcohol) (PVA) Modified with Methacrylate Groups:

A.1 Modification Using Glycidyl Methacrylate

The reaction of PVA with glycidyl methacrylate is depicted in Scheme 1 below:

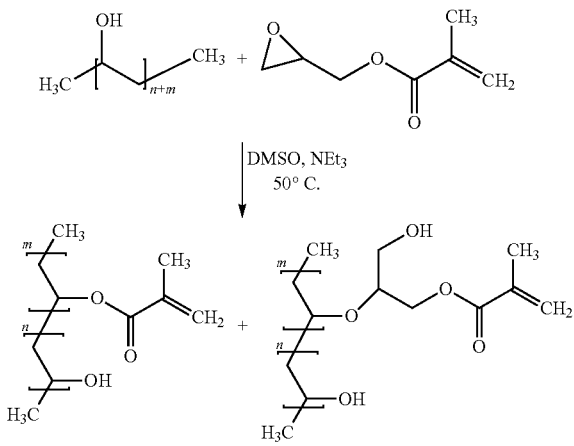

Scheme 1

50 ml of dry DMSO was added to a 100 ml round-bottom flask. The solvent was heated to 95° C. and stirred with a magnetic stirrer. 5 grams (113.6 mmol hydroxyl groups) of PVA (125 kg/mol) was added slowly to the hot solvent while stirring, and after four hours was totally immersed.

The solution was cooled to 70° C., and 0.7 gram (0.69 mmol) of triethylamine was added and totally immersed after 30 minutes. 0.5 gram (3.5 mmol) of glycidyl methacrylate was added slowly while stirring. The reaction mixture was incubated for one hour at 70° C., then cooled to 50° C. overnight, and then cooled to room temperature (~25° C.). The product was precipitated by pouring into 1 liter isopropanol, and vigorously mixing with a glass rod. The obtained white pellet was filtered, washed a few times with isopropanol, and dried for 12 hours in a vacuum, to yield PVA modified with methacrylate groups.

A.2 Modification Using 2-Isocyanoethyl Methacrylate

The reaction of PVA with 2-isocyanoethyl methacrylate is depicted in Scheme 2 below:

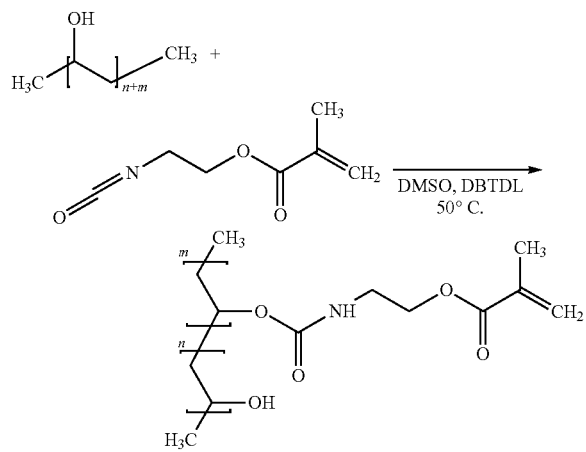

Scheme 2

50 ml of dry DMSO was added to a 100 ml round-bottom flask. The solvent was heated to 95° C. and stirred with a magnetic stirrer. 5 grams (113.6 mmol hydroxyl groups) of PVA (125 kg/mol) was added slowly to the hot solvent while stirring, and after four hours was totally immersed. The solution was cooled to 50° C. and 300 µl (0.5 mmol) of dibutyltin dilaurate (DBTDL) was added and totally immersed after 30 minutes. 0.5 gram (3.5 mmol) of 2-isocyanoethyl methacrylate was added slowly while stirring. The reaction mixture was incubated for 12 hours at 50° C., and then cooled to room temperature (~25° C.). The product was precipitated by pouring into 1 liter isopropanol, and vigorously mixing with a glass rod. The obtained white pellet was filtered, washed a few times with isopropanol, and dried for 12 hours in a vacuum, to yield PVA modified with methacrylate groups attached via a carbamate linking group.

A.3 Modification Using Methacrylic Anhydride

The reaction of PVA with methacrylic anhydride is depicted in Scheme 3 below:

Scheme 3

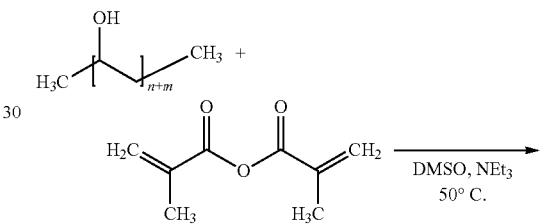

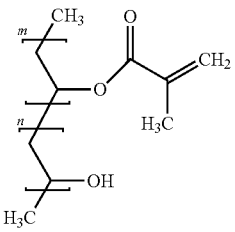

50 ml of dry DMSO was added to a 100 ml round-bottom flask. The solvent was heated to 95° C. and stirred with a magnetic stirrer. 5 grams (113.6 mmol hydroxyl groups) of PVA (125 kg/mol) was added slowly to the hot solvent while stirring, and after four hours was totally immersed. The solution was cooled to 50° C. and 500 µl (3.6 mmol) of triethylamine was added and totally immersed after 30 minutes. After cooling to room temperature (~25° C.), 1.2 gram (7.8 mmol) of methacrylic anhydride was added slowly while stirring. The reaction temperature was raised to 50° C. for 12 hours, then cooled to room temperature (~25° C.). The product was precipitated by pouring into 1 liter of isopropanol and vigorously mixing with a glass rod. The obtained white pellet was filtered, washed a few times with isopropanol, and dried for 12 hours in a vacuum, to yield PVA modified with methacrylate groups.

B. Preparation of Cross-Linked Poly(Vinyl Alcohol) (PVA) Sponge:

B.1 Cross-Linking with Formaldehyde

The cross-linking of PVA (modified with methacrylic groups; not shown) with formaldehyde is depicted in Scheme 4 below:

Scheme 4

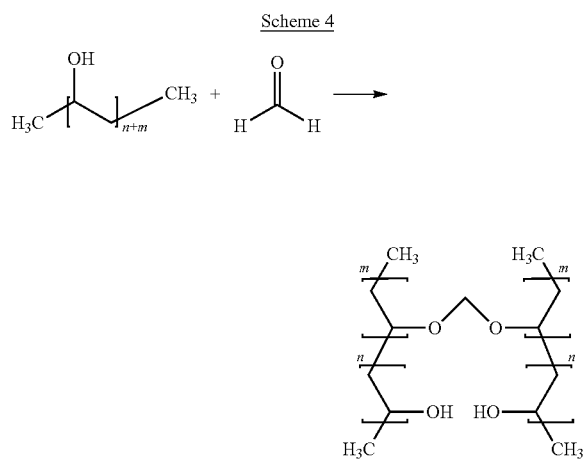

A 15% (by weight) solution of PVA modified with methacrylate groups (P(VAcoMA)), prepared as described hereinabove, was prepared by adding 4.5 grams of P(VAcoMA) to 30 ml of distilled water at 60° C. while stirring. After two hours the polymer was totally immersed. A fresh 20% (by weight) solution of formaldehyde was prepared by adding 1 gram paraformaldehyde (33.3 mmol formaldehyde monomers) to 5 ml of distilled water at 60° C. while stirring. 50 μl of 10% NaOH solution was added to complete immersion. 5 ml of the previously prepared 15% P(VAcoMA) solution was added to a 25 ml beaker placed in a cool water bath. Then 1.1 ml of concentrated sulfuric acid (or hydrochloric acid) was added slowly, followed by addition of 100 μl of the surfactant Triton™ X-405 (alternatively, Triton™ 100, Span™ 20, Tween™ 80, or Pluronic™ F127 were used), and then 1.2 ml of the previously prepared 20% formaldehyde solution. The solution was frothed using a frother for one minute, left for 45 minutes, and then frothed again for one more minute. The frothed solution was left for 24 hours at room temperature. The cross-linked product with a sponge structure was removed from the beaker, washed intensively with water, incubated for 2 hours in a sodium bicarbonate solution to neutralize the acidity, and then washed again with water, to yield a PVA sponge with methacrylate groups.

B.2 Cross-Linking with Butadiene Diepoxide

The cross-linking of PVA (modified with methacrylic groups; not shown) with butadiene diepoxide is depicted in Scheme 5 below:

Scheme 5

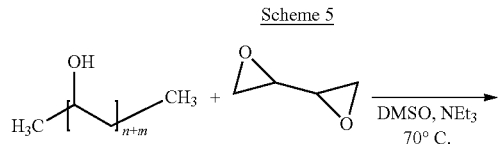

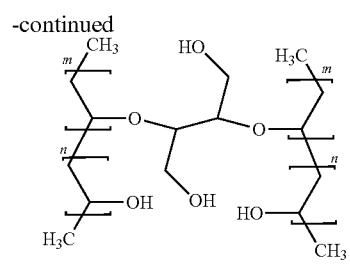

A 15% (by weight) solution of PVA modified with methacrylate groups P(VAcoMA), prepared as described hereinabove, was prepared by adding 4.5 grams of P(VAcoMA) to 30 ml of DMSO at 95° C. while stirring. After four hours the polymer was totally immersed. The solution was cooled to 70° C. and 0.56 gram (0.55 mmol) of triethylamine was added and totally immersed after 30 minutes. 5 ml of the previously prepared 15% P(VAcoMA) solution was added to a 25 ml beaker placed in a cool water bath, and 0.3 gram (3.5 mmol) of 1,3-butadiene diepoxide was added slowly while stirring. Then 0.35 gram of Pluronic™ P123 was added, followed by addition of 5 ml decane and 50 μl silicone oil. The solution was frothed using a frother for one minute followed by increasing the temperature to 70° C. for one hour, and then cooled to 50° C. overnight. The cross-linked product with a sponge structure was removed from the beaker and washed intensively with water, to yield a PVA sponge with methacrylate groups.

In addition, PVA sponges with methacrylate groups were prepared in a one-step process beginning from non-modified PVA (PVA without methacrylate groups). Cross-linking with butadiene diepoxide was effected according to procedures as described hereinabove, except that glycidyl methacrylate was also reacted with the PVA (according to procedures similar to those described in Section A.3 hereinabove), to yield a PVA sponge with methacrylate groups.

B.3 Cross-Linking with Hexamethylene Diisocyanate

The cross-linking of PVA (modified with methacrylic groups; not shown) with hexamethylene diisocyanate is depicted in Scheme 6 below:

Scheme 6

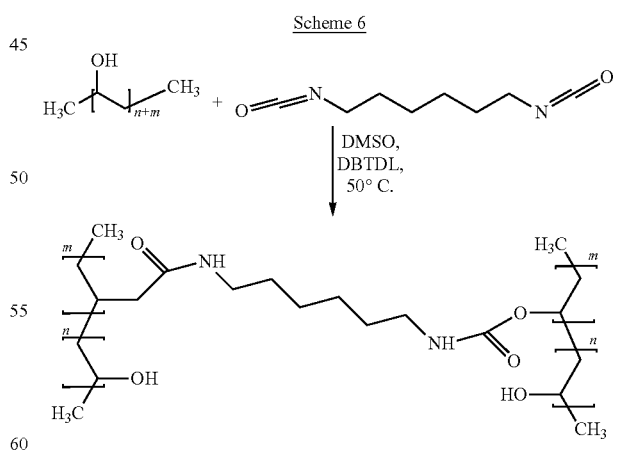

A 15% (by weight) solution of PVA modified with methacrylate groups (P(VAcoMA)), prepared as described hereinabove, was prepared by adding 4.5 grams of P(VAcoMA) to 30 ml of DMSO at 95° C. while stirring. After four hours the polymer was totally immersed. The solution was cooled to 50° C. and 300 μl (0.5 mmol) of dibutyltin dilaurate (DBTDL) was added and immersed after a few minutes. 5 ml of the previously prepared 15% P(VAcoMA) solution was added to a 25 ml beaker placed in a cool water bath, and 0.58 gram (3.5 mmol) of hexamethylene diisocyanate was added slowly while stirring. Next, 0.35 gram Pluronic™ P123 was added, followed by addition of 5 ml decane and 50 µl silicone oil. The solution was frothed using a frother for one minute, followed by increasing the temperature to 50° C. for four hours, then cooled to room temperature overnight. The cross-linked product with a sponge structure was removed from the beaker and washed intensively with water, to yield a PVA sponge with methacrylate groups.

In addition, PVA sponges with methacrylate groups were prepared in a one-step process beginning from non-modified PVA (PVA without methacrylate groups). Cross-linking with hexamethylene diisocyanate was effected according to procedures as described hereinabove, except that 2-isocyanatoethyl methacrylate was also reacted with the PVA (according to procedures similar to those described in Section A.2 hereinabove), to yield a PVA sponge with methacrylate groups attached via a carbamate linking group.

It is to be appreciated that the cross-linking procedures according to any one of Sections B.1-B.3 is optionally combined with the modification procedures according to any one of Sections A.1-A.3. In addition, alternative cross-linking rio modification procedures known in the art are optionally used instead of the cross-linking procedures according to any one of Sections B.1-B.3 or the modification procedures according to any one of Sections A.1-A.3, respectively.

It is expected that during the life of a patent maturing from this application many relevant methods will be developed.

As used herein with reference to quantity or value, the term "about" means "within ±25% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

What is claimed is:

1. A medical grade or non-medical grade implant, comprising a porous architecture which allows the passage of liquids, and a deformable body formed of a polymer cross-linked by a first cross-link, said polymer comprising functional groups capable of cross-linking to form a second cross-link; said body provided in a first configuration which is cross-linked to a second configuration upon application of a selected stimulus; wherein said selected stimulus causes said cross-linking of said functional groups, and wherein said first cross-link and said second cross-link are each a covalent crosslink.

2. The implant according to claim 1, wherein said stimulus is the initiator of the second cross-link between said first configuration to said second configuration.

3. The implant according to claim 1, wherein said cross-linking of said functional groups is cross-linking with each other.

4. The implant according to claim 1, wherein said cross-linking of said functional groups is cross-linking with another material.

5. The implant according to claim 1, wherein said stimulus is a liquid.

6. The implant according to claim 5, wherein the quantity of said liquid is from about 3% to about 100% of the total implant weight; and wherein the time required for said liquid to finish 80% of the cross-linking is from about 1 minutes to about 30 minutes.

7. The implant according to claim 1, wherein said stimulus comprises temperature and/or ultraviolet (UV) radiation.

8. The implant according to claim 7, wherein said temperature is from about 40 degrees Celsius to about 60 degrees Celsius; and wherein the time required for said stimulus to finish 80% of the cross-linking is from about 5 minutes to about 30 minutes.

9. The implant according to claim 7, wherein the time required for said UV to finish 80% of the cross-linking is from about 2 seconds to about 5 minutes.

10. The implant according to claim 1, wherein said stimulus is a monomer.

11. The implant according to claim 1, wherein in said first configuration said implant has an elastic modulus from about 0.01 to about 1 MPa.

12. The implant according to claim 1, wherein in said second configuration said device has an elastic modulus from about 2 to about 250 MPa.

13. The implant according to claim 1, wherein an elastic modulus of said second configuration is greater than an elastic modulus of said first configuration by a factor in a range of from about 10-fold to about 1000-fold.

14. The implant according to claim 1, wherein said body has an open cell structure having a porosity percentage from about 65% to about 85%.

15. The implant according to claim 1, wherein said body has an open cell structure which allows said body to be shrunk by compression, and said compression is stabilized by dehydration.

16. The implant according to claim 1, wherein the polymer has formula I:

[X]$_m$[X(-L-Y)]$_n$[X—Z-]$_p$  Formula I wherein:
m is zero or a positive integer;
n and p are each independently an integer which is at least 1,
wherein the sum of m, n and p is at least 10;
X is a backbone unit which forms a polymeric backbone;
L is absent or is a linking moiety;
Y is said functional group; and
Z is said first cross-link,
wherein L and Y together form a pendant group.

17. The implant according to claim 1, wherein the polymer comprises a plurality of backbone units having formula II:

—CR1R2-CR3A-  Formula II wherein:
A is selected from the group consisting of a covalent bond, R4, and a linking group, said linking group being selected from the group consisting of —O—, —S—, alkylene, arylene, cycloalkyl, heteroalicyclic, amine, sulfate, sulfonate, sulfonyl, sulfoxide, phosphate, phosphonyl, phosphinyl, alkoxy, aryloxy, thioalkoxy, thioaryloxy, azo, sulfonamide, carbonyl, thiocarbonyl, carboxy, carbonyl, thiocarbonyl, urea, thiourea, carbamyl, thiocarbamyl, amide, epoxide, cyanate and amino; and
R1-R4 are each independently selected from the group consisting of hydrogen, alkyl, alkenyl, alkynyl, cycloalkyl, aryl, heteroaryl, heteroalicyclic, amine, halide, sulfate, sulfonate, sulfonyl, sulfoxide, phosphate, phosphonyl, phosphinyl, hydroxy, alkoxy, aryloxy, thiohydroxy, thioalkoxy, thioaryloxy, cyano, nitro, azo, azide, sulfonamide, carbonyl, thiocarbonyl, carboxy, thiocarbamate, urea, thiourea, carbamate, amide, epoxide and hydrazine.

18. The implant according to claim 1, wherein said polymer is selected from the group consisting of poly(vinyl alcohol) (PVA), polyvinylamine (PVM), poly(vinyl chloride), a fluoropolymer, a polyester, a polyurethane, a polyurea, a silicone, and copolymers thereof.

19. The implant according to claim 1, wherein an average molecular weight of side chains in said polymer is no more than 50 Da.

20. The implant according to claim 1, wherein a weight ratio of side chains to backbone in said polymer is no more than 3:1 (side chain:backbone).

21. The implant according to claim 16, wherein said first cross-link comprises a residue selected from the group consisting of a formaldehyde residue, a dialdehyde residue, a dicarboxylic acid residue, a diepoxide residue, and a diisocyanate residue.

22. The implant according to claim 16, wherein an amount of said first cross-link in said polymer is in a range of from 1 cross-link per 100,000 monomeric units of said polymer to 1 cross-link per 100 monomeric units of said polymer and/or in a range of from 0.2 to 500 cross-links per 1 MDa of said polymer.

23. The implant according to claim 1, wherein said functional group is capable of cross-linking via polymerization.

24. The implant according to claim 1, wherein said functional group is selected from the group consisting of acryl, methacryl, cyanoacryl, and vinylsulfonyl.

25. The implant according to claim 1, wherein an amount of said functional group in said polymer is in a range of from 1 to 30 functional groups per 100 monomeric units of said polymer and/or in a range of from 200 to 6,000 functional groups per 1 MDa of said polymer.

26. The implant according to claim 16, wherein said polymer comprises at least 10 of said functional group per said first cross-link in said polymer.

* * * * *